United States Patent
Honkanen

(10) Patent No.: US 6,235,891 B1
(45) Date of Patent: May 22, 2001

(54) GLUCOCORTICOID RECEPTOR AGONIST AND DECREASED PP5

(75) Inventor: Richard E. Honkanen, Mobile, AL (US)

(73) Assignee: South Alabama Medical Science Foundation, Mobile, AL (US)

(*) Notice: Subject to any disclaimer, the term of this patent is extended or adjusted under 35 U.S.C. 154(b) by 0 days.

(21) Appl. No.: 09/282,736

(22) Filed: Mar. 31, 1999

(51) Int. Cl.[7] .............................. C12N 15/00; C12Q 1/68
(52) U.S. Cl. ...................... 536/24.5; 435/6; 435/91.1; 435/375; 435/325; 435/366; 536/23.1; 536/24.3
(58) Field of Search ................. 435/6, 91.1, 375, 435/325, 366; 536/23.1, 24.3, 24.5; 514/44

(56) References Cited

U.S. PATENT DOCUMENTS

| | | | |
|---|---|---|---|
| 5,034,506 | 7/1991 | Summerton et al. | 528/391 |
| 5,138,045 | 8/1992 | Cook et al. | 536/24.5 |
| 5,218,105 | 6/1993 | Cook et al. | 536/25.31 |
| 5,225,326 | 7/1993 | Bresser et al. | 435/6 |
| 5,459,255 | 10/1995 | Cook et al. | 536/27.13 |
| 5,591,721 | 1/1997 | Agrawal et al. | 514/44 |
| 5,767,113 | 6/1998 | Cohn et al. | 514/176 |

FOREIGN PATENT DOCUMENTS

| | | |
|---|---|---|
| WO 92/20823 | 11/1992 | (WO) . |
| WO 99/27134 | 6/1999 | (WO) . |
| WO 99/27136 | 6/1999 | (WO) . |

OTHER PUBLICATIONS

Branch, TIBS 23, pp. 45–50, Feb. 1998.*
Flanagan et al, Nature Biotech 17:48–52, Jan. 1999.*
Zuo et al, J. Biol Chem 273 (20) pp. 12250–12258, May 15, 1998.*
Tian et al, J. Biol Chem 273 (22) pp. 13531–13536, May 29, 1998.*
Agarwal, M.L., et al., Proc Natl Acad Sci USA 92:8493–8497 (1995).
Ammala, C., et al., Proc Natl Acad Sci USA 91:4343–4347 (1994).
Bastians, H., et al., J Cell Sci 109:2865 (1996).
Bialojan, A., et al., Biochem J 256:283 (1988).
Brewis, N.D., et al., EMBO J 12:987 (1993).
Cairns, J., et al., J of Bio Chem 269(12):9176–9183 (1994).
Chen, M.X., et al., EMBO J 13(18):4278–4290 (1994).
Chernova, O. B., et al., Trends Bio Sci 20:431 (1995).
Cohen, P., Annu Rev Biochem 58:453 (1989).
Cohen, P., et al., FEBS Lett 268:355 (1990).
Cohen, P., et al., Trends Bio Sci 15:98 (1990).
Cohen, P., TIBS 22: 245–251 (1997).
Duttaroy, A., et al., J Cell Biochem 64:434 (1997).

(List continued on next page.)

Primary Examiner—Remy Yucel
Assistant Examiner—M Schmidt
(74) Attorney, Agent, or Firm—Braman & Rogalskyj, LLP

(57) ABSTRACT

A composition comprises a glucocorticoid receptor agonist and a compound which decreases levels of active human serine/threonine protein phosphatase 5 protein in cells. The glucocorticoid receptor agonist is dexamethasone and the compound is an antisense oligonucleotide of about 8 to 50 nucleotides in length which is targeted to a nucleic acid encoding human serine/threonine protein phosphatase 5. The composition is useful in a method of enhancing glucocorticoid activity, and in a method of enhancing the inhibition of hyperproliferation of cells where the inhibition is by contacting the cells with a compound which decreases levels of active human serine/threonine protein phosphatase 5 protein in cells. The compound is thus useful to enhance glucocorticoid therapy and to enhance inhibition of hyperproliferation relating to PP5.

7 Claims, 5 Drawing Sheets

OTHER PUBLICATIONS

Dynlacht, B.D., Nature 389:149 (1997).
Egloff, M.P. et al., J Mol Biol 254:942 (1995).
Elledge, S.J., et al., Curr Opin Cell Biol 6:847 (1994).
Gomyo, Y., et al., Cancer 79:2067 (1997).
Gottlieb, T.M., et al., Biochem Biophys Acta 1287:77 (1996).
Gu., Y., et al., Nature 366:707 (1993).
Harper, J.W., et al., Mol Biol Cell 6:387 (1995).
Honkanen, R.E., et al., J Biol Chem 265:19401 (1990).
Honkanen, R.E., et al., Toxicon 32:339 (1994).
Hsiao, M., et al., Biochem Biophys Res Commun 233:329 (1997).
Hunter, T., et al., Cell 79:573 (1994).
Lamb, J.R., et al., Trends in Bio Sci 20:257 (1995).
Macleod, K.F., et al., Genes Dev 9:935 (1995).
Peter, M., et al., Cell 79:181 (1994).
Scully, R., et al., Cell 90:425 (1997).
Sherr, C.J., Cell 79:551 (1994).
Sogawa, K., et al., Cancer Letters 89:1–6 (1995).
Sogawa, K., et al., Res Commun Mole Path Pharm 86(3):375–378 (1994).
Somasundaram, K., et al., Nature 389:187 (1997).
Wera, S., et al., Biochem J 311:17–29 (1995).
Xiong, Y., et al., Nature 366:701 (1993).
Yamada, T., et al., Res Comm Mole Path Pharm 86(1):125–128 (1994).
Yin, Y., et al., Cell 70:937 (1992).
Zeng, Y.X., et al., Oncogene 12:1557 (1996).
El–Deiry, W.S., et al., Cell 75:817–825 (1993).
Harper, J.W., et al., Cell 75:805–816 (1993).
Becker, W., et al., J Bio Chem 269(36):22586–22592 (1994).
Chinkers, M., Proc Natl Acad Sci USA 91:11075–11079 (1994).
Skinner, J., et al., J Bio Chem 272(36):22464–22471 (1997).
Ashihara et al., Methods in Enzymology LVIII:248–262 (1979).
Berge et al., J Pharm Sci 66(1):1–19 (1977).
Chiang et al., J Biol Chem 266(27):18162–18171 (1991).
Sanghvi, in Crooke, et al., Eds "Antisense Research and Applications", CRC Press, Boca Raton, pp. 276–278 (1993).
De Mesmaeker et al., Acc Chem Res 28:366–374 (1995).
Kabanov et al., FEBS Letters 259(2):327–330 (1990).
Kawasaki et al., J Med Chem 36:831–841 (1993).
Letsinger et al., Proc Natl Acad Sci USA 86:6553–6556 (1989).
Manoharan et al., Annals NY Acad Sci 660:306–309 (1992).
Manoharan et al., Nucleosides & Nucleotides 14(3–5):969–973 (1995).
Manoharan et al., Tetrahedron Letters 36(21):3651–3654 (1995).
Manoharan et al., Bioorganic & Med Chem Letters 4(8):1053–1060 (1994).
Manoharan et al., Bioorganic & Med Chem Letters 3(12):2765–2770 (1993).
Nielsen et al., Science 254:1497–1500 (1991).
Oberhauser et al., Nucl Acids Res 20(3):533–538 (1992).
Saison–Behmoaras et al., EMBO J 10(5):1111–1118 (1991).
Sambrook et al., "Molecular Cloning—A Laboratory Manual", Cold Spring Harbor Laboratory Press, Cold Spring Harbor 2:10.59–10.61 (1989).
Sanghvi et al., Nucl Acids Res 21(14):3197–3203 (1993).
Svinarchuk et al., Biochimie 75:49–54 (1993).
von Pierre Martin, Helv Chim Acta 78:486–504 (1995).
Barker et al., Biochimical et Biophysica Acta. 1178:228–233 (1993).
Milligan et al., J of Medicinal Chemistry 36:1923–1937 (1993).
Cohen, Tibitech 10:87–91 (1992).
Yong et al., Genomics 29:533–536 (1995).
Xu et al., Biochemical and Biophysical Research Communications 218:514–517 (1996).
Brewis et al., Biochinical et Biophysica Acta. 1171:231–233 (1992).
Norman et al., Mammalian Genome 5:41–45 (1994).
Branch, TIBS 23:45–50 (1998).
Gewirtz et al., PNAS 83:3161–3163 (1996).
Rojanasakul, Advanced Drug Delivery Reviews 18:115–131 (1996).
J.H. Clark, et al., in Wilson et al., Eds "Williams Textbook of Endocrinology", W.B. Saunders Company, pp. 77–78 (1992).
D.N. Orth, et al., in Wilson et a., Eds "Williams Textbook of Endocrinology", W.B. Saunders Company, pp. 570–575 (1992).

* cited by examiner

GLUCOCORTICOID RECEPTOR AGONIST AND DECREASED PP5

This invention was made with support from the U.S. Government under National Institutes of Health Grant No. CA60750. The U.S. Government may have certain rights in this invention.

FIELD OF THE INVENTION

This invention relates generally to compositions and methods for enhancing glucocorticoid therapy and for enhancing the inhibition of hyperproliferation of cells, and more particularly to a composition comprising a glucocorticoid receptor agonist and a compound which decreases levels of active human serine/threonine protein phosphatase 5 in cells.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Abnormal proliferative or hyperproliferative conditions include hypoproliferative disorders such as cancer, tumors and hyperplasias, including smooth muscle cell proliferation in the blood vessels (such as stenosis or restenosis following angiopathy). In these conditions, a means to control or inhibit (decrease) hyperproliferation is desirable. Many types of cellular mechanisms/molecules have been or could be associated with regulation of cellular proliferation. For example, the reversible phosphorylation of proteins on serine and threonine residues is a major intracellular control mechanism that regulates cell proliferation. The phosphorylation state of a protein is controlled by kinases, which phosphorylate proteins, and phosphatases, which dephosphorylate proteins. A number of families and types of protein phosphatases exist, including tyrosine phosphatases and serine/threonine protein phosphatases (PPs). An increase in expression of certain PPs has been described in several tumor types. Therefore, one could speculate that inhibitors of PP expression may have an effect on tumors (such as an anti-proliferative effect).

Small molecule inhibitors of protein phosphatases have been used to study PP function. The best characterized of these is okadaic acid, which is the causative agent of diarrhetic shellfish poisoning. It is a potent inhibitor of PP2A and PP1 and a much (roughly a thousandfold) less potent inhibitor of PP2B. Other inhibitors of one or more PPs include tautomycin, cyclosporin A, dinophysistoxin, calyculin, microcystin, nodularin and cantharidin (Cairns et al. 1994; Wera and Hemmings 1995).

One could also speculate that antisense oligonucleotides could be used to inhibit PP expression. Antisense oligonucleotides have been safely administered to humans and clinical trials of several antisense oligonucleotide drugs, targeted both to viral and cellular gene products, are presently underway.

In addition to the role of PPs in cell proliferation, glucocorticoids are another example of a cellular molecule which has been associated with cellular proliferation. Glucocorticoids are known to induce growth arrest in the G1-phase of the cell cycle in a variety of cells, both in vivo or in vitro, and have been shown to be useful in the treatment of certain cancers. The glucocorticoid receptor (GR) belongs to an important class of transcription factors that alter the expression of target genes in response to a specific hormone signal. Accumulated evidence indicates that receptor associated proteins play key roles in regulating glucocorticoid signaling. The list of cellular proteins that can bind and co-purify with the GR is constantly expanding. PP5 has been shown to be one of the proteins that co-immunoprecipitated with GR (Chen et al, 1996).

These two, PP5 and glucocorticoids, are merely two examples of many cellular mechanisms/molecules which have been associated with regulation of cellular proliferation. A need continues to exist to elucidate further means to regulate cell proliferation, in particular to decrease cell proliferation in hyperproliferative disorders.

Glucocorticoids are also used for their anti-inflammatory effect on the skin, joints, and tendons. They are important for treatment of disorders where inflammation is thought to be caused by immune system activity, such as rheumatoid arthritis, inflammatory bowel disease, glomerulonephritis, and connective tissue diseases like systemic lupus erythematosus. They are used to treat asthma and are widely used with other drugs to prevent the rejection of organ transplants. Some cancers of the blood (leukemias) and lymphatic system (lymphomas) may also respond to corticosteroid drugs. A method of enhancing the beneficial effects of glucocorticoid therapy in these instances would always be desirable.

SUMMARY OF THE INVENTION

The subject invention addresses these needs by providing a composition comprising a glucocorticoid receptor agonist and a compound which decreases levels of active human serine/threonine protein phosphatase 5 protein in cells. Preferably, the compound which decreases levels of active (functional) human serine/threonine protein phosphatase 5 protein in cells is an antisense oligonucleotide targeted to a nucleic acid encoding human serine/threonine protein phosphatase 5. The composition of the subject invention can be used to enhance glucocorticoid therapy and to enhance the inhibition of hyperproliferation of cells. In one embodiment, the composition is used in a method of enhancing glucocorticoid activity in cells which comprises contacting cells with an amount of the composition of the subject invention effective to enhance glucocorticoid activity in the cells. In another embodiment, the composition is used in a method of enhancing the inhibition of hyperproliferation of cells, wherein the inhibition is by contacting the cells with a compound which decreases levels of active human serine/threonine protein phosphatase 5 protein in cells, which method comprises contacting the cells with an amount of the composition of the subject invention effective to enhance the inhibition of hyperproliferation of the cells. The composition of the subject invention can thus be used to enhance glucocorticoid therapies in conditions such as inflammations and asthma, and to enhance therapy in hyperproliferative disorders such as cancer based on decreasing levels of active PP5.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION OF THE INVENTION

Figure 1A:
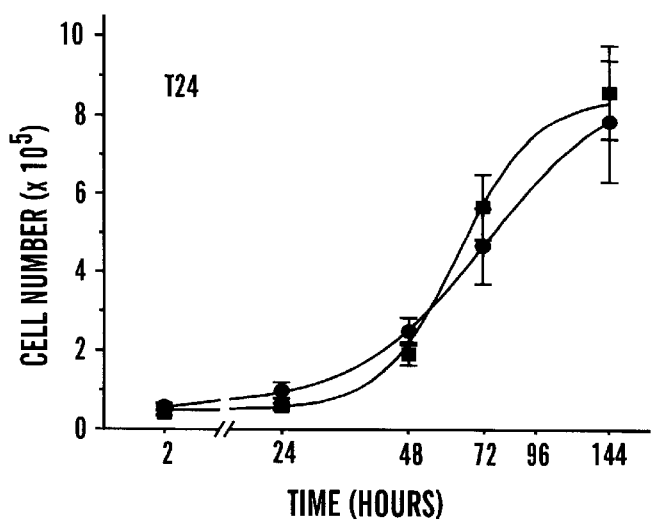
FIGS. 1A–1D illustrate that the antiproliferative effect of dexamethasone correlates with the presence of wild type p53 and the expression of $p21^{Waf1/Cip1}$ mRNA.

The subject invention provides a composition comprising a glucocorticoid receptor agonist and a compound which decreases levels of active human serine/threonine protein phosphatase 5 (PP5) protein in cells.

Levels of active (functional) PP5 protein in the cells can be decreased by various compounds, at the gene and protein levels. In one embodiment, the levels are decreased by decreasing PP5 gene expression of the PP5 protein in the cells. This can be accomplished by exposing the cells to a compound which decreases PP5 gene expression of the PP5 protein. The compound could be, for example, an antisense oligonucleotide targeted to a nucleic acid encoding PP5. This aspect of the subject invention is discussed in further detail below, where particular antisense oligonucleotides targeted to the PP5 gene are disclosed as being about 8 to 50 nucleotides in length (for example, the antisense oligonucleotides having a nucleotide sequence selected from the group consisting of: SEQ ID NO:1, SEQ ID NO:3, SEQ ID NO:4, SEQ ID NO:5, SEQ ID NO:6, SEQ ID NO:8, and SEQ ID NO:9). Preferably, the antisense oligonucleotide is targeted to a translation initiation site, coding region, or 3' untranslated region of mRNA encoding the PP5.

In a similar embodiment, the compound which decreases PP5 gene expression of the PP5 protein could be a ribozyme, which is a special category of antisense RNA molecule having a recognition sequence complementary to the mRNA encoding the PP5. A ribozyme not only complexes with a target sequence via complementary antisense sequences, but also catalyzes the hydrolysis, or cleavage, of the template mRNA molecule. The expression of the PP5 protein is therefore prevented.

Other compounds for decreasing PP5 gene expression could be compounds which cause site-directed mutagenesis of the PP5 gene (thereby preventing expression of the PP5 protein), or compounds used in various gene therapy techniques (in a broad context, a "vector" which incorporates into the cell and which alters the PP5 gene of the cell is a "compound" which decreases PP5 gene expression of the PP5 protein).

Levels of active PP5 protein in the cell can also be decreased by exposing the cells to compounds which are inhibitors of the PP5 protein. Currently known inhibitors of PP5 include, for example, okadaic acid, microcystin, cantharidin, and fostriecin. Other inhibitors of the PP5 protein could also readily be identified by various screening methods used in the art. In addition to chemical inhibitors, peptide and other small molecule inhibitors could also be identified with currently known screening methods (for example, using phage display libraries and other peptide screening methods). These inhibitors of PP5 protein effectively decrease levels of active PP5 protein in the cell by, for example, binding to or blocking or otherwise interfering with PP5 function.

As used herein, glucocorticoids refer to the steroid hormone glucocorticoids. The glucocorticoid receptor (GR) refers to the receptor for the steroid hormone glucocorticoids. An "agonistl" is a compound which interacts with the steroid hormone receptor to promote a transcriptional response. "Glucocorticoids" are agonists for the glucocorticoid receptor. Compounds which mimic glucocorticoids would also be defined as glucocorticoid receptor agonists. A presently preferred glucocorticoid receptor agonist is dexamethasone. Other common glucocorticoid receptor agonists include cortisol, cortisone, prednisolone, prednisone, methylprednisolone, trimcinolone, hydrocortisone, and corticosterone. As used herein, glucocorticoid is intended to include, for example, the following generic and brand name corticosteroids: cortisone (CORTONE ACETATE, ADRESON, ALTESONA, CORTELAN, CORTISTAB, CORTISYL, CORTOGEN, CORTONE, SCHEROSON); dexamethasone—oral (DECADRON-ORAL, DEXAMETH, DEXONE, HEXADROL-ORAL, DEXAMETHASONE INTENSOL, DEXONE 0.5, DEXONE 0.75, DEXONE 1.5, DEXONE 4); hydrocortisone—oral (CORTEF, HYDROCORTONE); hydrocortisone cypionate (CORTEF ORAL SUSPENSION); methylprednisolone—oral (MEDROL-ORAL); prednisolone—oral (PRELONE, DELTA-CORTEF, PEDIAPRED, ADNISOLONE, CORTALONE, DELTACORTRIL, DELTASOLONE, DELTASTAB, DI-ADRESON F, ENCORTOLONE, HYDROCORTANCYL, MEDISOLONE, METICORTELONE, OPREDSONE, PANAAFCORTELONE, PRECORTISYL, PRENISOLONA, SCHERISOLONA, SCHERISOLONE); prednisone (DELTASONE, LIQUID PRED, METICORTEN, ORASONE 1, ORASONE 5, ORASONE 10, ORASONE 20, ORASONE 50, PREDNICEN-M, PREDNISONE INTENSOL, STERAPRED, STERAPRED DS, ADASONE, CARTANCYL, COLISONE, CORDROL, CORTAN, DACORTIN, DECORTIN, DECORTISYL, DELCORTIN, DELLACORT, DELTA-DOME, DELTACORTENE, DELTISONA, DIADRESON, ECONOSONE, ENCORTON, FERNISONE, NISONA, NOVOPREDNISONE, PANAFCORT, PANASOL, PARACORT, PARMENISON, PEHACORT, PREDELTIN, PREDNICORT, PREDNICOT, PREDNIDIB, PREDNIMENT, RECTODELT, ULTRACORTEN, WINPRED); triamcinolone—oral (KENACORT, ARISTOCORT, ATOLONE, SHOLOG A, TRAMACORT-D, TRI-MED, TRIAMCOT, TRISTO-PLEX, TRYLONE D, U-TRI-LONE). U.S. Pat. No. 5,767,113 to Cohn et al. discloses a method for identifying compounds that have the dual ability of acting as glucocorticoid receptor agonists and of inhibiting the P-glycoprotein efflux pump (thereby reducing multidrug resistance). Any compounds so identified can be used as glucocorticoid receptor agonists in the composition of the subject invention.

The subject invention is based on the discovery of a relationship between PP5 and glucocorticoids. In particular, the data shows that when PP5 is inhibited, the binding of the activated glucocorticoid receptor to DNA is enhanced. This enhancement results in enhanced induction or suppression of downstream genes. Thus, one can enhance the effects of glucocorticoid therapy by decreasing levels of active PP5. One can also enhance the inhibition of hyperproliferation of cells caused by compounds which decrease levels of active PP5, by adding glucocorticoid therapy. The combination of glucocorticoid therapy (a glucocorticoid receptor agonist) with a compound which decreases levels of active PP5 protein in cells results in roughly 20× enhancement of the effect of either alone.

The invention thus provides a method of enhancing glucocorticoid activity in cells. The method comprises contacting cells with an amount of the composition of the subject invention effective to enhance glucocorticoid activity in the cells. Glucocorticoids work by binding the glucocorticoid receptor which as an "activated receptor" then induces some genes to turn on and also keeps other genes from turning on (suppression). Enhancement of glucocorticoid activity thus refers to enhanced induction and/or suppression of downstream genes. The method of the subject invention is thus applicable in enhancement of the effectiveness of all glucocorticoid therapies. Glucocorticoids are principally used for their anti-inflammatory effect on the skin, joints, and tendons. They are important for treatment of disorders where inflammation is thought to be caused by immune system activity, such as rheumatoid arthritis, inflammatory bowel disease, glomerulonephritis, and connective tissue diseases like systemic lupus erythmatosus. They are used to treat asthma and are widely used with other drugs to prevent the rejection of organ transplants. Some cancers of the blood (leukemias) and lymphatic system (lymphomas) may also respond to corticosteroid drugs. The method of the subject invention can thus be used to enhance glucocorticoid therapy in any of these examples.

Likewise, the data herein establishes that enhancement of therapies relating to PP5 can be accomplished by combining such therapies with glucocorticoid therapy. Therapies relating to PP5 primarily involve abnormal proliferative or hyperproliferative disorders. Examples of abnormal proliferative conditions are hyperproliferative disorders such as cancers, tumors and hyperplasias, including smooth muscle cell proliferation in the blood vessels, such as stenosis or restenosis following angioplasty. Decreasing levels of active PP5 in these conditions results in inhibition of hyperproliferation. The inhibition is enhanced by combining the decreasing levels of actie PP5 with glucocorticoid therapy.

The subject invention thus also provides a method of enhancing the inhibition of hyperproliferation of cells, wherein the inhibition is by contacting the cells with a compound which decreases levels of active PP5 protein in the cell, which method comprises contacting the cells with an amount of the composition of the subject invention effective to enhance the inhibition of hyperproliferation of the cells. As used herein, to inhibit hyperproliferation refers to decreasing or eliminating hyperproliferation.

In the methods of the invention, tissues or cells are contacted with the composition of the subject invention. In the context of this invention, to "contact" tissues or cells with a composition means to add the composition, usually in a liquid carrier, to a cell suspension or tissue sample, either in vitro or ex vivo, or to administer the composition to cells or tissues within an animal (including humans).

The formulation of therapeutic compositions and their subsequent administration is believed to be within the skill in the art. In general, for therapeutics, a patient suspected of needing such therapy is given a composition in accordance with the invention, commonly in a pharmaceutically acceptable carrier, in amounts and for periods which will vary depending upon the nature of the particular disease, its severity and the patient's overall condition. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration. For oral administration, it has been found that oligonucleotides for use in the compositions with at least one 2'-substituted ribonucleotide are particularly useful because of their absortion and distribution characteristics. U.S. Pat. No. 5,591,721 (Agrawal et al.). Oligonucleotides with at least one 2'-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

In addition to such pharmaceutical carriers, cationic lipids may be included in the formulation to facilitate uptake. One such composition shown to facilitate uptake is Lipofectin (BRL, Bethesda Md.).

Since many steroids are essentially insoluble in water, except when prepared in extremely dilute solution they should be formulated as organic esters (e.g., acetates, butyrates, dipropionates, valerates), which have very limited solubility, or as salts (e.g., hydrochlorides, sodium phosphates, sodium succinates), which are freely soluble. Except for the salts, many steroids are preferably used in topical creams and for intramuscular and intra-articular injection as opposed to intravenous use. The insoluble free alcohols can be prepared as tablets for oral administration.

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual compositions, and can generally be calculated based on $IC_{50}$'s or $EC_{50}$'s in in vitro and in vivo animal studies. For example, given the molecular weight of compound (derived from oligonucleotide sequence and chemical structure) and an effective dose such as an $IC_{50}$, for example (derived experimentally), a dose in mg/kg is routinely calculated.

In particular regard to the dosing of corticosteroids, dosage and route of administration generally depend on the disorder being treated. Parenteral administration of high doses may be warranted in emergencies, such as septic shock and severe acute asthma. Intravenous boluses of gram doses of methylprednisolone have been used in transplant rejection and in some autoimmune diseases. Oral preparations are generally used for chronic therapy. Intra-articular injection is often used for joint inflammation, inhalation of aerosolized steroids is often used for asthma, and topical application is often used for inflammatory dermatological disorders. A more detailed discussion of dosage regimens of corticosteroids is provided in Orth et al. 1992 and in Schimmer and Parker 1996.

THE ANTISENSE OLIGONUCLEOTIDES

The present invention employs oligonucleotides targeted to nucleic acids encoding serine/threonine protein phosphatases. The relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding a protein phosphatase; in other words, a protein phosphatase gene or mRNA expressed from a protein phosphatase gene. The targeting process also includes determination of a site or sites within the nucleic acid sequence for the oligonucleotide interaction to occur such that the desired effect—modulation of gene expression—will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of protein phosphatase gene expression is presently the preferred form of modulation. This modulation can be measured in ways which are routine in the art, for example by Northern blot assay of mRNA expression or Western blot assay of protein expression as taught in the examples of the instant application. Effects on cell proliferation can also be measured, as taught in the examples of the instant application. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In accordance with the subject invention, oligonucleotides are provided which are targeted to mRNA encoding serine/threonine protein phosphatase 5 (PP5). In accordance with this invention, persons of ordinary skill in the art will understand that mRNA includes not only the coding region which carries the information to encode a protein using the three letter genetic code, including the translation start and stop codons, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. In preferred embodiments, the oligonucleotide is targeted to a translation initiation site (AUG codon) or sequences in the coding region, 5' untranslated region or 3'-untranslated region of mRNA encoding human PP5. The functions of mRNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with PP expression.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Certain preferred oligonucleotides of this invention are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Consequently, comparable results can often be obtained with shorter oligonucleotides when chimeric oligos are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case a nucleic acid encoding a protein phosphatase) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In a more preferred embodiment, the region of the oligonucleotide which is modified to increase PP mRNA binding affinity comprises at least one nucleotide modified at the 2' position of the sugar, most preferably a 2'-O-alkyl, 2'-O-alkyl-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of PP gene expression. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. A discussion of antisense oligonucleotides and some desirable modifications can be found in De Mesmaeker et al. (1995).

Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, $CH_2$—$N(CH_3)$—O—$CH_2$ [known as a methylene (methylimino) or MMI backbone], $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones, wherein the native phosphodiester backbone is represented as O—P—O—$CH_2$). The amide backbones disclosed by De Mesmaeker et al. (1995) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al. 1991). Oligonucleotides may also contain one or more substituted sugar moieties. Preferred oligonucleotides comprise one of the following at the 2' position: OH, SH, $SCH_3$, F, OCN, $OCH_3OCH_3$, $OCH_3O$ $(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy (also known in the art as O-alkyl-O-alkyl), substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—$CH_2CH_2OCH_3$, also known as 2'-O—(2-methoxyethyl) or 2'-MOE] (Martin et al., Helv. Chim. Acta, 1995, 78, 486). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (also referred to as 5-methyl-2'deoxycytosine and often referred to in the art as 5-me-C), 5-hydroxymethylcytosine (HMC), glycosyl HMC and gentobiosyl HMC, as well as synthetic nucleobases, e.g., 2-aminoadenine, 2-thiouracil, 2-thiothymine, 5-bromouracil, 5-hydroxymethyluracil, 8-azaguanine, 7-deazaguanine, $N^6$ (6-aminohexyl)adenine and 2,6-diaminopurine (Kornberg 1980; Gebeyehu et al. 1987). A "universal" base known in the art, e.g., inosine, may be included. 5-me-C substitutions have been shown to increase nucleic acid duplex stability by 0.6–1.2° C. (Sanghvi 1993) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al. 1989), cholic acid (Manoharan et al. 1994), a thioether, e.g., hexyl-S-tritylthiol (Manoharan et al. 1992); (Manoharan et al. 1993), a thiocholesterol (Oberhauser et al. 1992), an aliphatic chain, e.g., dodecandiol or undecyl residues (Saison-Behmoaras et al. 1991; Kabanov et al. 1990; Svinarchuk et al. 1993), a phospholipid, a polyamine or a polyethylene glycol chain (Manoharan et al. 1995a), or adamantane acetic acid (Manoharan et al. 1995b). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes chimeric oligonucleotides as hereinbefore defined.

The antisense oligonucleotides of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the oligonucleotides of the invention, pharmaceutically acceptable salts of such prodrugs, and other bioequivalents.

Prodrugs: The oligonucleotides of the invention may additionally or alternatively be prepared to be delivered in a prodrug form. The term prodrug indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

Pharmaceutically Acceptable Salts: The term pharmaceutically acceptable salts refers to physiologically and pharmaceutically acceptable salts of the oligonucleotides of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al. 1997). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides in accordance with this invention preferably are from about 8 to about 50 nucleotides in length. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

EXAMPLE 1

Synthesis and Characterization of Oligonucleotides

Unmodified oligodeoxynucleotides are synthesized on an automated DNA synthesizer (Applied Biosystems model 380B) using standard phosphoramidite chemistry with oxidation by iodine. $\beta$-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides were synthesized using 2'-methoxy $\beta$-cyanoethyldiisopropyl-phosphoramidites (Chemgenes, Needham Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides were synthesized as described in Kawasaki et al. (1993). Briefly, the protected nucleoside $N^6$-benzoyl-2'-deoxy-2'-fluoroadenosine was synthesized utilizing commercially available 9-$\beta$-D-arabinofuranosyladenine as starting material and by modifying literature procedures whereby the 2'-$\alpha$-fluoro atom is introduced by a $S_N2$-displacement of a 2'-$\beta$-O-trifyl group. Thus $N^6$-benzoyl-9-$\beta$-D-arabinofuranosyladenine was selectively protected in moderate yield as the 3',5'-ditetrahydropyranyl (THP) intermediate. Deprotection of the THP and $N^6$-benzoyl groups was accomplished using standard methodologies and standard methods were used to obtain the 5'-dimethoxytrityl-(DMT) and 5'-DMT-3'-phosphoramidite intermediates.

The synthesis of 2'-deoxy-2'-fluoroguanosine was accomplished using tetraisopropyldisiloxanyl (TPDS) protected 9-β-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a literature procedure in which 2, 2'-anhydro-1-β-D-arabinofuranosyluracil was treated with 70% hydrogen fluoride-pyridine. Standard procedures were used to obtain the 5'-DMT and 5'-DMT-3'phosphoramidites.

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3'phosphoramidites.

2'-(2-methoxyethyl)-modified amidites are synthesized according to Martin (1995). For ease of synthesis, the last nucleotide was a deoxynucleotide. 2'-O—$CH_2CH_2OCH_3$-cytosines may be 5-methyl cytosines.

Synthesis of 5-Methyl Cytosine Monomers
2,2'-Anhydro[1-(β-D-arabinofuranosyl)-5-methyluridine]:

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.
2'-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.
2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).
3'-O-Acetyl-2'-O-methoxyethyl-5'-O-dimethoxytrityl-5-methyluridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).
3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.
2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite:

N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al. 1993) using commercially available phosphoramidites (Glen Research, Sterling Va. or ChemGenes, Needham Mass.).

Oligonucleotides having methylene(methylimino) backbones are synthesized according to U.S. Pat. No. 5,378,825, which is incorporated herein in its entirety. Other nitrogen-containing backbones are synthesized according to WO 92/20823 which is also incorporated herein in its entirety.

Oligonucleotides having amide backbones are synthesized according to De Mesmaeker et al. (1995). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to Nielsen et al. (1991).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al. (1991). Results obtained with HPLC-purified material were similar to those obtained with non-HPLC purified material.

EXAMPLE 2

Oligonucleotide Inhibition of PP5 Expression

The oligonucleotides shown in Table 1 were designed using the Genbank sequences HSSERTHRP (Genbank accession number X92121), HSRNAPPP5 (Genbank accession number X89416) and PPP5C (Genbank accession number U25174), synthesized and tested for inhibition of PP5 mRNA expression in A549 cells using a Northern blot assay. All oligonucleotides shown in Table 1 are chimeric oligonucleotides with central 2'-deoxy "gaps," which have phosphorothioate backbones, flanked on both sides by 2'-methoxyethoxy (2'-MOE) "wings" (shown in bold), which have phosphodiester backbones. All cytosines in the 2'-MOE wings are 5-methylcytosines.

In the initial screen, A549 cells were treated with oligonucleotides at a concentration of 300 nM oligonucleotide for four hours in the presence of 20 mg/ml lipofectin. Results were normalized and expressed as a percent of control. The effect of each oligonucleotide on levels of PP5 mRNA, expressed as approximate percent inhibition compared to control, is shown in Table 1. In this initial screen, oligonucleotides giving a reduction of PP5 mRNA of approximately 50% or greater were considered active. According to this criterion, oligonucleotides 14493, 14494, 14495, 14496, 14498, 14499 and 14504 were found to be active. These sequences (SEQ ID NO: 1, 2, 3, 4, 6, 7 and 12, respectively, SEQ ID Nos shown in bold in Table 1) are therefore preferred. Of these, oligonucleotides 14493, 14498 and 14504 (SEQ ID NO: 1, 6 and 12, respectively) showed at least 70% inhibition of PP5 mRNA in this assay and are highly active.

EXAMPLE 3

Additional Oligonucleotides Targeted to PP5

Additional oligonucleotides targeted to PP5 and having SEQ ID NO: 12 were synthesized. These are chimeric oligonucleotides having slightly wider deoxy gaps (and shorter 2'-MOE wings, shown in bold) than ISIS 14504. These oligonucleotides are shown in Table 2, along with ISIS 15521, a mismatch control.

These oligonucleotides differ in their backbone composition; ISIS 15523 is uniformly phosphorothioate (P=S) and ISIS 15534 is a mixed backbone compound with a phosphodiester backbone (P=O) in the wings and phosphorothioate (P=S) in the deoxy gap. ISIS 15521, the mismatch control, is also a mixed backbone compound with phosphodiester wings and a phosphorothiate gap.

These oligonucleotides were tested for their ability to reduce PP5 mRNA levels in A549 cells, using oligonucleotide doses of 25 to 500 nM. ISIS 15523 demonstrated an IC$_{50}$ of approximately 100 nM, and ISIS 15534 demonstrated an IC$_{50}$ of approximately 135 nM. The mismatch control, ISIS 15521, did not inhibit PP5 mRNA levels by more than 20% at any of the doses tested.

EXAMPLE 4

Effect of Antisense Inhibition of PP5 Expression on Cell Proliferation

A549 cells were treated with ISIS 15534 or its scrambled control, ISIS 15521 at a concentration of 300 nM. Each day for the next 5 days, viable cells were counted. The scrambled control oligonucleotide, ISIS 15521, was approximately equivalent to untreated control on all 5 days. In contrast, the cells treated with ISIS 15534 showed markedly decreased proliferation compared to untreated cells. On days 2, 3, 4 and 5, ISIS 15534-treated cells showed a decrease in proliferation of 55%, 75%, 89% and 55%, respectively, compared to control.

EXAMPLE 5

Effect of Antisense Inhibition of PP5 Expression on DNA Replication

A549 cells were treated with ISIS 15534 or its scrambled control, ISIS 15521 at a concentration of 300 nM. Cells were pulse-labeled with [$^3$H]-thymidine for 5 hours at intervals over the next five days. Cells were lysed and [$^3$H]-thymidine incorporation (indicative of DNA synthesis) was determined by liquid scintillation counting. The scrambled control oligonucleotide, ISIS 15521, was approximately equivalent to untreated control on all 5 days. In contrast, the cells treated with ISIS 15534 showed markedly decreased thymidine incorporation compared to untreated cells. On days 2, 3, 4 and 5, ISIS 15534-treated cells showed a decrease in [$^3$H]-thymidine incorporation of approximately 85%, 88% and 62%, respectively, compared to control. By day 5 [$^3$H]-thymidine incorporation was approximately equivalent in treated and untreated cells.

EXAMPLE 6

Additional Oligonucleotides Targeted to PP5

An additional oligonucleotide targeted to PP5 and having SEQ ID NO: 1 was synthesized. This compound, ISIS 15516 has a phosphorothioate backbone and is a chimeric oligonucleotide having a slightly wider deoxy gap (and shorter 2'-MOE wings, shown in bold) than ISIS 14493. These oligonucleotides are shown in Table 3, along with ISIS 15517, a mismatch control with a mixed backbone (P=S in the gap, P=O in the wings).

ISIS 15516 and 15517 oligonucleotides were tested for their ability to reduce PP5 mRNA levels in RINm5f cells. Dose response curves were generated for oligonucleotide doses of 25 to 500 nM. ISIS 15516 demonstrated an IC$_{50}$ of approximately 135 nM. The scrambled control, ISIS 15517, gave less than 10% reduction of PP5 mRNA levels at any dose tested.

RINm5f cells are an insulin-secreting insulinoma rat cell line. Previous studies indicate that there is a correlation between cell growth, insulin secretion, calcium channel activity and phosphatases in RINm5f cells. In both humans and rat, calcium channels are phosphorylated, and phosphorylation is believed to keep the channel closed (i.e., phosphorylation causes a decrease in the frequency and/or duration of channel opening). There is substantial evidence that calcium channels are involved in the regulation of insulin secretion. Calcium channel blockers such as nifedipine and verapamil are used in the treatment of cardiac disorders, such as angina, congestive heart failure and certain arrhythmias, as well as hypertension. Thus agents that affect calcium channels, particularly calcium channel blockers, are believed to be therapeutically useful.

The antisense oligonucleotide ISIS 15516 (SEQ ID NO: 1), targeted to the AUG region of human PP5, was tested in RINm5f cells for its effect on calcium channels, using standard patch-clamp techniques. Because the human and rat PP5 mRNA sequences are identical in the target region of this oligonucleotide, ISIS 15516 is perfectly complementary to this portion of the rat PP5 sequence. Treatment of RINm5f cells with a 300 nM concentration of ISIS 15516 indicated that this compound decreases calcium currents in these cells. The mismatch control oligonucleotide, ISIS 15517, did not show this effect. Since inhibition of PP5 expression by ISIS 15516 is now shown to decrease calcium current density, it is believed that this compound and other inhibitors of PP5 may be useful as calcium channel blockers, for example in treatment of cardiac conditions.

EXAMPLE 7

Northern Blot Analysis of Inhibition of Protein Phosphatase mRNA Expression

The human lung tumor cell line A549 was obtained from the American Type Culture Collection (Rockville Md.) and were grown in DMEM (Gibco BRL, Gaithersburg Md.), supplemented with 10% fetal calf. Cells were seeded on 60 mm plates. When they reached 70% confluency, they were washed with DMEM and 1 ml of DMEM containing 15 μg/ml DOTMA/DOPE (Lipofectin®, GIBCO-BRL) and oligonucleotide at desired concentration was added. Duplicate dishes were used for each treatment condition. After 4 hours of treatment at 37°, cells were washed and cultured in fresh DMEM containing 10% fetal bovine serum for an additional 17 hours. Cells were then harvested and total RNA was extracted with TRIzol Reagent (GIBCO-BRL) according to manufacturer's protocol. Total RNA (20 μg) was fractionated on a 1% agarose gel containing formaldehyde, and transferred to a DURLON-UV (Stratagene) nylon membrane. Following UV crosslinking, the filters were hybridized with the appropriate protein phosphatase probe. The $^{32}$P-labeled human PP cDNA probes are generated with DECAPrime® DNA Labeling Kit (Ambion) according to the manufacturer's protocol. Hybridization was performed in a hybridization solution containing 50% formamide at 42° for 16 hours. This was followed by two low stringency washes (2×SSC) at room temperature and two high stringency washes (0.1×SSC/0.5% SDS) at 55° C. Hybridization signals were visualized by autoradiography, and filters were then stripped and reprobed with a $^{32}$P-labeled glyceraldehyde-3-phosphate dehydrogenase (GAPDH) probe to confirm equal loading. The densities of hybridization signals were measured with the NIH Image program (ImagePC).

EXAMPLE 8

Antisense Inhibition of Cell Proliferation

A549 cells were seeded in 12-well tissue culture plates at about 50% confluence in DMEM containing 10% fetal bovine serum. The next day, cells were treated with the PP5-specific antisense oligonucleotide, ISIS 15534, or its scrambled control, ISIS 15521, at a final concentration of 300 nM as described in Example 7. On each of the following 5 days, cultures from three wells of each treatment gruop were trypsinized, collected and counted. Cell viability was determined by trypan blue staining, and the results given are the mean of three independent experiments.

EXAMPLE 9

Measurement of [$^3$H]-thymine Incorporation

A 549 cells were subcultured in 24-well tissue culture plates and treated with the PP5-specific antisense oligonucleotide ISIS 15534 or its scrambled control, ISIS 15521 at a final concentration of 300 nM as described in Example 7. At timed intervals during the next 5 days, cells were pulse-labeled with [$^3$H]-thymidine (0.5 µCi/ml) for 5 hours. The cells were then lysed, and [$^3$H]-thymidine incorporation was determined by liquid scintillation counting using standard methods (Baserga et al. 1979). The results given are the mean of three independent experiments.

EXAMPLE 10

Effect of Oligonucleotides on Calcium Channels

The effect of antisense oligonucleotides on calcium channels was tested in RINm5f cells. This is an insulin-secreting insulinoma rat cell line available from the American Type Culture Collection, Rockville Md. Calcium currents were measured using standard patch-clamp techniques to measure ion conductance. These techniques are described in, for example, Ammala et al. (1994).

EXAMPLE 11

A549 Xenografts

A549 cells are obtained from the American Type Culture Collection (Bethesda Md.) and grown in T-75 flasks until 65–75% confluent. 5×10$^6$ A549 cells are implanted subcutaneously in the inner thigh of nude mice. The PP5-specific antisense oligonucleotide, ISIS 15534, or its scrambled control, ISIS 15521, suspended in saline, are administered once daily by intravenous injection at doses ranging from 0.006 to 6.0 mg/kg. Resulting tumors are measured on days 9, 12, 17 and 21 and tumor volumes are calculated.

EXAMPLE 12

Detection of Protein Phosphatase Expression

PP-specific oligonucleotides are radiolabeled after synthesis by $^{32}$P labeling at the 5' end with polynucleotide kinase. (Sambrook et al. 1989). Radiolabeled oligonucleotides are contacted with tissue or cell samples suspected of PP expression, such as tumor biopsy samples, under conditions in which specific hybridization can occur, and the sample is washed to remove unbound oligonucleotide. Radioactivity remaining in the sample indicates bound oligonucleotide and is quantitated using a scintillation counter or other routine means.

Analogous assays for fluorescent detection of PP expression use oligonucleotides of the invention which are labeled with fluorescein or other fluorescent tags. Labeled DNA oligonucleotides are synthesized on an automated DNA synthesizer (Applied Biosystems model 380B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling Va.). Incubation of oligonucleotide and biological sample is carried out as described for radiolabeled oligonucleotides except that instead of a scintillation counter, a fluorimeter or fluorescence microscope is used to detect the fluorescence which indicates PP expression.

EXAMPLE 13

Combination of Antisense and Glucocorticoid Receptor Agonist

MATERIALS AND METHODS

Materials

All tissue culture medium, DOTMA/DOPE lipofectin®, and TRIzol® reagents, SuperScript™ II RNase H Reverse Transcriptase were from GIBCO BRL (Grand Island, N.Y.). FCS was from HyCone Laboratories (Logan, Utah). DECAprime™ II DNA labeling kit were purchased from Ambion Inc. (Austin, Tex.). QIAEX DNA absorption resin was from QIAGEN. PP5 specific antiserum generated from the c-terminal peptide of human PP5 was from Immunodynamics. HPR-conjugated secondary antibodies, phosphorylase kinase (EC 2.7.1.38), protein kinase A (3':5'-cyclic AMP dependent), phosphorylase b (EC 2.4.1.1), crude histone (type 2AS), p-nitrophenyl phosphate (pNPP) were obtained from Sigma (St. Louis, Mo.). [α-$^{32}$P]-dATP was from Dupont NEN (Boston, Mass.). [γ-$^{32}$P]-dATP was from New England Nuclear. Formamide and Dextran sulfate were purchased from Fisher Scientific, Fair Lawn, N.J. All chemicals were purchased from Sigma unless otherwise indicated. Human retina cDNA and human retina cDNA library constructed in λgt11 were kindly provided by Dr. S. J. Pittler at Dept. Biochemistry and Molecular biology, U. South AL. (Mobile, Ala.). Phosphorothioate oligodeoxynucleotides and 2'-O-methyl phosphorothioate oligodeoxynucleotides were synthesized at ISIS Pharmaceuticals (Carlsbad, Calif.). pBlueScript® SK phagemid cloning vector was from Stratagene (La Jolla, Calif.). Prokaryotic expression vectors pKK223-3 and pSE were from Pharmacia Biotech (Piscataway, N.J.).

p53 consensus oligonucleotide, anti-p53 mouse monoclonal antibody DO-1, protein A—agarose, normal mouse serum were purchased from Santa Cruz Biotechnology Inc. (Santa Cruz, Calif.). [3H]-thymidine was from DuPont-NEN (Boston, Mass.). TR9-7 cells were kindly provided by Drs. G. Stark and M. Agarwal (Cleveland Clinic Foundation, Cleveland, Ohio).

GR binding consensus oligonucleotide was purchased from Santa Cruz Biotechnology Inc. (Santa Cruz, Calif.). Luciferase assay kit were from Promega. GRE reporter plasmid, MMTV-Luc, and internal control plasmid, pSV-β-GAL, and anti-human GR antibody were kindly provided by Dr. J. G. Scammell at Dept. Pharmacology, U. South AL (Mobile, Ala.).

Cell Culture

Human A549 lung carcinoma cells were obtained from the American Type Culture Collection (ATCC). A549 cells were maintained in Dulbecco's modified Eagle's medium (DMEM) containing 10% fetal calf serum (FCS) and routinely passed when 90–95% confluent. T-24 and RINmF5 cells were obtained from American Type Culture Collection (ATCC), and were maintained in McCoys A5 or RPMI 1640 media, respectively, supplemented with 10% FCS. TR9-7 cells were derived from p53$^{-/-}$ human fibroblasts (MDAH041) and contain tetracycline-regulated transactivator and operator plasmids to control the expression of wild-type p53 (Agarwal et al., 1995). TR9-7 cells were maintained in DMEM containing 10% FCS and the indicated amount of tetracycline.

Antisense Oligodeoxynucleotide Treatment

For oligonucleotide treatment, cells were plated in 60 mm dishes and cultured in DMEM containing 10% FCS. When the cells were about 70% confluent, they were treated with ODNs as previously described (Dean et al., 1994; Dean et al., 1997). Briefly, cells were washed with serum-free DMEM. A solution (1 ml) of serum-free DMEM containing the ODNs at the indicated concentration and 15 µg/ml DOTMA/DOPE Lipofectin® was then added into each dish. After incubating the cells at 37° C. for 4 hours, the cells were washed and cultured in fresh DMEM containing 10% FCS for another 16 to 18 hours.

Analysis of Cell Growth

A549 cells were seeded in 12-well tissue culture plates at a density of $5.0 \times 10^4$ cell/dish. On the next day, the cells were treated with PP5 specific antisense oligonucleotides (ISIS 15534) or the scrambled mismatch control (ISIS 15521) at a final concentration of 300 nM as described above. On each of the next five days, the cell cultures were treated briefly with trypsin to detach the cells from the dish (three wells from each test group). The number of cells was then determined by counting using a hemacytometer. Cell viability was determined with trypan blue staining. The percentage of viable cells was calculated by dividing the number of cells excluding trypan blue by the total number of cells, and the results are reported as the mean +/− SD of data collected from three independent experiments.

Receptor Binding Assay

A [$^3$H]-dexamethasone radioligand-binding assay and Scatchard analysis was used to determine the effect of antisense ODN on GR-binding capability in A549 cells. Follwing ODN treatment, as described above, cells were washed with DMEM and incubated with increasing concentrations of [$^3$H]-dexamethasone for 60 minutes at 37° C. Following incubation, the tubes were centrifuged and 20 ml of supernatant was counted in a beta spectrometer to measure free dexamethasone concentration. The cell pellet, which measures whole cell dexamethasone concentration, was next rinsed, dried, and counted in a beta spectrometer.

All values obtained were corrected for nonsaturable binding for each respective concentration. Saturation-binding analysis was performed assuming a linear binding plot of the bound divided by the free [$^3$H]-dexamethasone concentration vs the amount bound and extrapolating to determine the amount at an infinite free hormone concentration. A least-squares linear regression fit was used to define both receptor sites per cell and binding affinity.

Inmmunocytochemistry

Cells were plated onto 60 mm dishes at a concentration of $0.5 \times 10^6$ cell per dish and treated with antisense ODN or control ODN as described above. Mitotic cells were harvested by "mitotic shake off" method and deposited by centrifugation onto poly-L-lysine-coated coverslips. The cells were then fixed by immersion of the cover slips in −20° C. methanol for 6–8 min and processed for immunofluorescence microscopy. Anti-human GR antibody was used at 1 µg/ml dilution. FITC-labeled secondary antibodies (Boehringer Mannheim Biochemicals) were used at a 1:200 dilution. After processing, coverslips were mounted in PBS: glycerol (1:1) containing 25 µg/ml HOECHST 33258 dye. Cells were observed using an Axiovert 35 M microscope (Carl Zeiss, Inc.).

Luciferase Assay

Transfections and luciferase assays were conducted as described by Jones et al. (1996) using a mouse mammary tumor virus-luciferase reporter plasmid (MMTV-Luc). (Jones et al. 1996). Briefly, A549 cells were transfected in serum-free medium with 1 µg MMTV-Luc plasmid DNA per 60 mm dish using 15 µg/ml Lipofectin. ODNs were added into the transfection media wherever applicable. After a 4-hour incubation, the medium was replaced with fresh complete culture medium, and the cells were cultured overnight. The cells were then treated with different amounts of dexamethasone for two hours. Cell extracts were prepared with reporter lysis buffer (Promega). Cell extracts were assayed for luciferase activity at room temperature by placing 150 µl cell lysate in an assay cuvette, adding 100 µl of assay buffer containing 30 mM Tricine (pH 7.8), 3 mM ATP, 15 mM MgSO$_4$, and 10 mM DTT, and injecting 100 µl 1 mM D-luciferin into the sample. Light production was measured for 20 seconds at 562 nm using a Monolight 2010 luminometer (Analytical Luminescence Lab., San Diego, Calif.). To control for difference in transfection efficiency, contransfections were performed with 1 µg of a plasmid encoding β-galactosidase controlled by the SV40 virus promoter (pSV-β-GAL). β-GAL activity was measured in 150 µl cell extracts using the β-Galactosidase Enzyme Assay System (Promega).

Northern Analysis

The cells were harvested, and total RNA was extracted with TRIzol® Reagent according to the methods of the manufacturer. Total RNA (20 µg) was fractionated on 1% agarose gels containing formaldehyde and transferred to DURLON-UV nylon membranes (Stratagene). Following UV cross-linking, the filters were hybridized with a [$\alpha^{32}$P] probe for human PP5. The human PP5 cDNA probe was generated from the full length coding region of PP5 and [$\alpha^{32}$P]-dATP was labeled with DECAprime® DNA Labeling Kit according to the manufacturer's protocol. Hybridization was performed in the presence of 50% formamide, 0.1 M Pipes, 0.8 M NaCl, 5×Denhardt's solution, 100 µg/ml denatured herring sperm DNA, $1 \times 10^6$ cpm/ml [$\alpha$-$^{32}$P]-labeled probe and 10% dextran sulfate at 42° C. for 16 hours. Following hybridization, the membrane was subjected to two low stringency washes (2×SSC) at room temperature and then two high stringency washes (0.1×SSC/0.5% SDS) at 55° C. Hybridization was visualized by autoradiography, and the filters were then stripped and reprobed with a [$^{32}$P] labeled glyceraldehyde-3-phosphate dehydrogenase (G3PDH) cDNA probe to confirm equal loading. Quantification of hybridization signals was achieved by analysis of the scanned autoradiograms using the NIH Image program (ImagePC).

The human PP5 cDNA probe was generated from the full length clone of PP5 by PCR using a nested primer pair (RH36, SEQ ID NO:16: 5'-ATGGCGATGGCGGAGGG-CGAGAGGACTGAGTGTGC-3' and RH41, SEQ ID NO:17: 5'-TCACATCATTCCTAGCACCAGCAGCG-3'). The human p21$^{Waf1/Cip1}$ cDNA probe was generated from human retina cDNA by PCR using a nested primer pair (RH87, SEQ ID NO:18: 5'-ATGTCAGAACCGGCTGG-GGATGTC-3', and RH88, SEQ ID NO:19: 5'-GGGCTTCCTCTTGGAGAAGATCAG-3'). The human p53 CDNA probe was generated from human retina CDNA by PCR using a nested primer pair (SEQ ID NO:20: 5'-CCAGAATGCCAGAGGCTGCT-3', and SEQ ID NO:21: 5'-TCATCCAAATACTCCACACG-3').

Gel Mobility Shift Assay

Nuclear extracts and gel mobility shift assays were conducted as previously described (Li et al. 1991) with slight modifications (Zuo et al. 1998). Briefly, A549 cells were cultured in 60 mm dishes and treated with ISIS 15521 or ISIS 15534 antisense oligonucleotides (Zuo et al. 1998) three dishes per group. Six hours after treatment, the cells were collected, washed with ice-cold PBS, and incubated in buffer A (10 mM HEPES, pH 7.9, 10 mM KCl, 0.1 mM EDTA, 0.1 mM EGTA, 1 mM DTT, 0.5 mM PMSF) at 4° C. for 15 minutes. The cells were then lysed by adding 25 µl 10% NP-40 and vigorous vortexing for 10 seconds. Nuclei were precipitated by centrifugation, resuspended in ice-cold buffer B (20 mM HEPES, pH 7.9, 0.4 M NaCl, 1 mM EDTA, 1 mM EGTA, 1 mM DTT, 1 mM PMSF), incubated at 4° C. for 60 minutes with gentle shaking, and then subjected to centrifugation at 4° C. for 5 minutes. The supernatant was collected, aliquoted, and stored at −80° C.

Binding reactions were performed by incubating 10 µg of each nuclear extract with 1 ng of [$^{32}$P]end labeled GR-consensus sequence oligonucleotide (Santa Cruz) (SEQ ID NO:22: 5'-AGA GGA TCT GTA CAG GAT GTT CTA GAT-3') and 1 μg of Poly(dI-dC) in binding buffer (20 mM HEPES, pH 7.9, 0.25 M EDTA, 50 μM KCl, 1 mM DTT, 1 mM PMSF, 10% (v/v) glycerol) at room temperature for 20 minutes. Anti-GR rabbit polyclonal antibody (1 μg; Santa Cruz) was added to the indicated reactions to identify GR and incubated at room temperature for 30 minutes. Samples were separated by electrophoresis on a 5% polyacrylamide gel containing Tris borate/EDTA buffer and visualized by autoradiography.

Immunoprecipitation

Immunoprecipitation of p53 protein. A549 cells were cultured in 60 mm dishes until the cell cultures were about 80% confluent, washed with PBS and placed for 1 hour in phosphate-free DMEM containing 5% fetal bovine serum. The cell cultures were then treated with 100 nM dexamethasone or 300 nM ISIS 15521 or ISIS 15534 as described previously (Zuo et al. 1998), three dishes per group, and [$^{32}$P] phosphate (0.2 mCi/ml) was added to the media. Six hours after treatment, the cells were collected, washed with ice-cold PBS and stored at −80° C. prior to analysis. Cell lysates were prepared by incubating the thawed cells at 4° C. for 1 hour in a buffer containing 1% Nonidet P-40, 0.5% sodium deoxycholate, 150 mM sodium chloride, 5 mM EDTA, 1 mM sodium pyrophosphate, 50 mM sodium fluoride, 1 mM PMSF, 5 μg/ml leupeptin, 5 μg/ml aprotinin, and 50 mM Tris-HCl, pH 8.0. Insoluble debris was removed by centrifugation at 3000 rpm at 4° C. for 15 minutes. The supernatants were collected and pre-cleared by incubation with 1.2 μg of normal IgG (Santa Cruz) and 20 μl of protein A-agarose for 1 hour at 4° C., followed by centrifugation at 1500 rpm at 4° C. for 5 minutes. Equal amounts of protein from each pre-cleared lysate were incubated in the presence of 1 μg of anti-p53 mouse monoclonal antibody DO-1 (Santa Cruz) for 2 hours at 4° C. Twenty μl of protein A-agarose was added to the mixture, which was then incubated for 16 hours at 4° C. with rocking. The agarose beads were collected by centrifugation and washed five times with 1 ml of ice-cold cell lysis buffer. After the final wash, the pellet was resuspended in 40 μl 2× sample buffer, boiled for 3 minutes, and separated by SDS-PAGE on 10% gels. The bands were visualized by autoradiography.

SDS-PAGE Analysis and Western Blotting

Western analysis was performed essentially as described previously using polyclonal rabbit antibodies generated against a synthetic 15 amino acid peptide identical to the C-terminal region of PP5 (Honkanen et al. 1991) or using anti-p53 mouse monoclonal antibody D01. Briefly, A549 cells grown in T-75 flasks were washed twice with ice cold PBS. Then, 250 μl of lysis buffer was added to each flask. The extract was then subjected to centrifugation at 13,000×G for 5 minutes, and an aliquot of the supernatant was removed for protein determination. The remaining supernatant was added to an equal volume of 2× sample buffer (120 mM Tris-HCL, pH 7.4, 200 mM Dithiothreitol, 20% glycerol, 4% SDS and 0.02% bromphenol blue). Protein was determined using a Bio-Rad protein quantitation assay (Bio-Rad), with bovine serum albumin as standards. Typically 25–50 μg of protein was then separated by electrophoresis on 10% SDS-polyacrylamide gels. Each gel was run under a condition of constant current and was stopped when the blue dye-front just reached the bottom of the gel. The gel was then stained with 0.2% Coomassie blue for 4–5 hours in a staining solution containing 50% methanol and 10% acetic acid, and then destained with several changes of destaining solution containing 25% methanol and 7% acetic acid.

For immunoblotting experiment, the protein from the polyacrylamide gel was electrophoretically transferred to Immobilon-P (Millipore) and the membrane was blocked for 1 hour with Tris-HCl, pH 7.4, containing 150 mM NaCl and 5% nonfat milk. To detect protein, membranes were incubated with anti-PP5 or anti-p53 antibody diluted in Tris-HCl (pH 7.6), 150 mM NaCl, 0.2% Tween 20 (TBST) containing 2% nonfat milk for 18 hours at 4° C. The membrane was then washed, and the bound primary antibody was detected employing ECL western blotting detection reagents (Amersham Life Science, Buckinghamshire, England), following the protocols of the manufacturer.

RESULTS

Figure 1B:
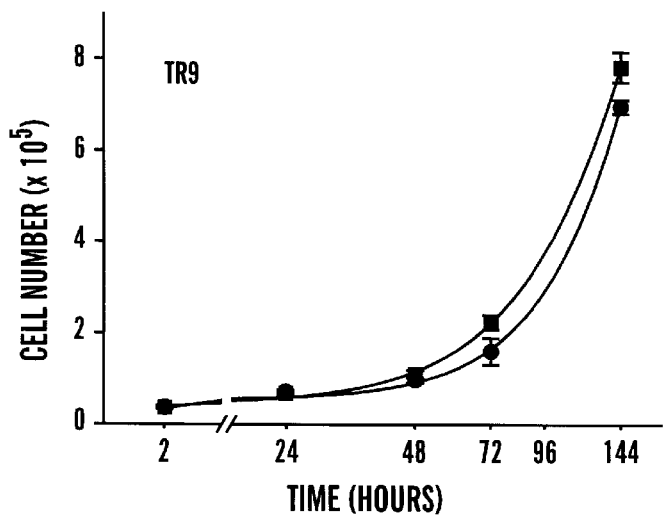
Figure 1C:
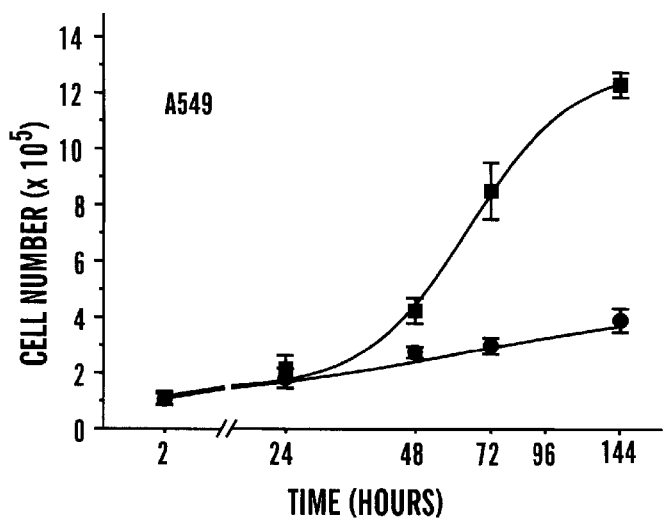
Figure 1D:
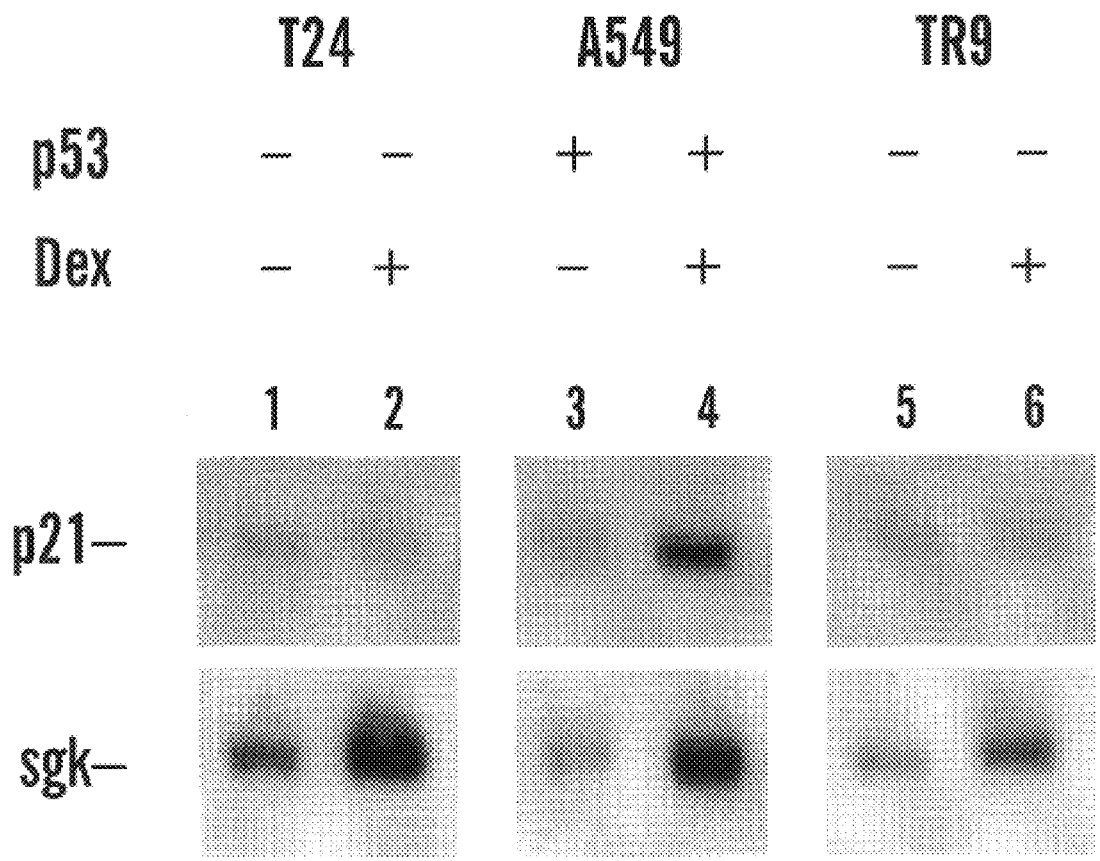

Initial comparison of the effects induced by dexamethasone, a potent glucocorticoid receptor agonist, to those produced by ISIS 15534, a potent inhibitor of PP5 expression (Zuo et al. 1998) revealed many similarities in three different human cell lines (FIGS. 1A–1C). Treatment of p53 wild-type lung carcinoma (A549) cells with either ISIS 15534 (Zuo et al. 1998) or dexamethasone produced growth arrest (FIG. 1C), with a concomitant increase in the expression of p21$^{Waf1/Cip1}$ (FIG. 1D). In contrast, in p53-defective bladder carcinoma (T-24) cells or p53-null (p53$^{−/−}$) fibroblasts (TR9) neither ISIS 15534 nor dexamethasone induced the expression of p21$^{Waf1/Cip1}$ or growth arrest (FIGS. 1A and 1B, respectively). Binding studies indicated that all three cell lines expressed GR (intact cell binding studies were conducted with [$^3$H]dexamethasone essentially as described previously by Reynolds et al. 1997), and dexamethasone induced the expression of serum/glucocorticoid inducible protein kinase (sgk) in all three cell lines (FIG. 1D). This suggests that all three cell lines contain functional GR.

The antiproliferative effect of dexamethasone correlates with the presence of wild type p53 and the expression of p21$^{Waf1/Cip1}$ mRNA. Referring to FIGS. 1A–1C, the effect of dexamethasone on cell proliferation in p53-defective T-24 human bladder carcinoma, p53-null TR9 human fibroblasts (Webster et al. 1993; Maiyar et al. 1996), and p53 wild-type A549 human lung carcinoma cells was determined by treating cells in log-phase growth with a single dose of 100 nM dexamethasone and counting the number of cells in treated (•) and untreated (■) cultures for six consecutive days following treatment. Each point represents the mean of triplicate dishes with error bars representing SE. Under similar conditions, treatment with ISIS 15534, a potent inhibitor of PP5 gene expression, inhibited growth in A459 but not T-24 or TR9 cells (Zuo et al. 1998). Referring to FIG. 1D, a comparison of p21$^{Waf1/Cip1}$ (p21) and serum glucocorticoid inducible protein kinase (sgk) mRNA levels in p53 competent (Lanes 3, 4) and p53 deficient (Lanes 1, 2, 5, 6) cell cultures after dexamethasone treatment is shown. Cell cultures in logphase growth were treated with 100 nM dexamethasone (+) or vehicle alone as a control (−). After 24 hours total mRNA was prepared and analyzed for p21 and sgk mRNA levels by Northern analysis.

To explore the relationship of PP5, p53 and glucocorticoid receptor activation further, we employed a stable cell line (TR9-7) derived from p53$^{−/−}$ human fibroblasts (MDAH041) that contain tetracycline-regulated transactivator and operator plasmids to control the expression of wild-type p53 (Agarwal et al. 1995). In TR9-7 cells, the overexpression of p53 alone is sufficient for the induction of p21$^{Waf1/Cip1}$ and G1-growth arrest (Reynolds et al. 1997), and neither the inhibition of PP5 expression nor the activation of GR with dexamethasone induces growth arrest in the absence of p53 (Zuo et al. 1998; Reynolds et al. 1997).

However, when the expression of wild type p53 is induced and maintained at a low level, which does not induce the expression of p21$^{Waf1/Cip1}$ or elicit growth arrest on its own and is comparable to the basal amount of p53 expressed in non-stressed fibroblasts, the hyperphosphorylation of p53 produced by the inhibition of PP5 expression results in the induction of p21$^{Waf1/Cip1}$ and G1-growth arrest (Zuo et al. 1998). Thus, PP5 appears to regulate the phosphorylation state of p53, which in turn regulates the ability of p53 to induce the expression of p21$^{Waf1/Cip1}$ (Zuo et al. 1998; Chernov et al. 1998).

Transient transfection studies conducted in BDS1 hepatoma cells, which are acutely sensitive to the antiproliferative effects of glucocorticoids, revealed that although dexamethasone stimulated p21$^{Waf1/Cip1}$ promoter activity is decreased when the p53 binding element is removed from the promoter region of a p21-reporter plasmid, dexamethasone treatment of cells transfected with the p53-binding domain deficient reporter plasmids still produced a significant increase in luciferase activity (Cram et al. 1998). This suggests that glucocorticoid receptor (GR) mediated induction of p21$^{Waf1/Cip1}$ can occur via a p53-independent mechanism (Cram et al. 1998). In A549 cells, glucocorticoid-induced expression of p21$^{Waf1/Cip1}$ and growth arrest occurs without an increase in the amount of p53 protein, indicating that increased p53 expression is not needed for glucocorticoid mediated induction of p21$^{Waf1/Cip1}$. However, not a single cell line, or report, was found where dexamethasone was capable of inducing growth arrest if p53 was absent or defective. Furthermore, glucocorticoids elicit the expression of serine/threonine protein kinases, such as sgk (Webster et al. 1993; Maiyar et al. 1996), which raises the possibility that glucocorticoids increase p53 transactivation by inducing a cellular response that results in the hyperphosphorylation of p53. This may not require an increase in the amount of p53 protein and is not likely to be detected with p21-reporter plasmids lacking a p53 binding domain.

Figures 2A, 2B, 2C:
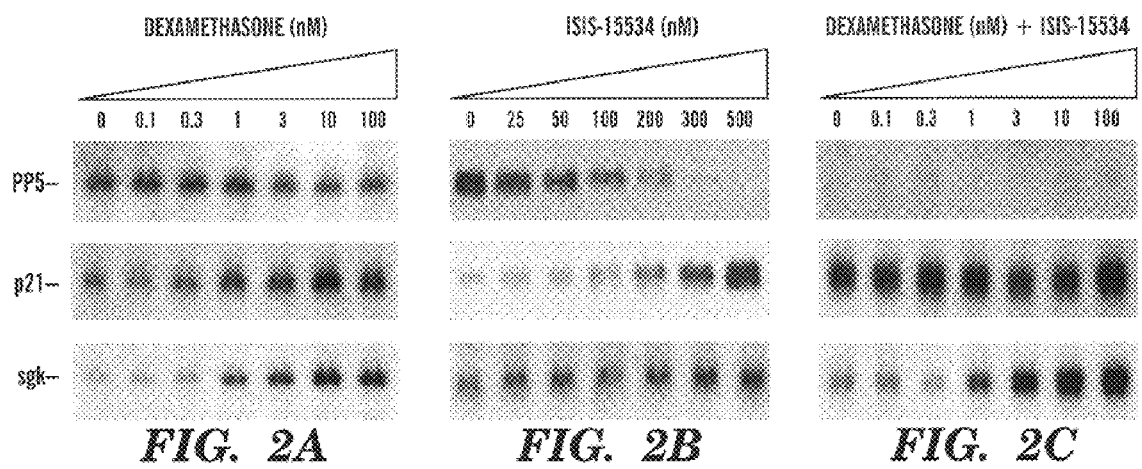
FIGS. 2A–2E illustrate Northern blot analyses of A549 cells following treatment with dexamethasone and/or ISIS 15534.

To explore the possibility that dexamethasone induces the expression of a protein kinase that participates in the regulation of p53 transcriptional activity, Northern analysis and immunoprecipitation studies were employed to detect changes in the amount and phosphorylation status of p53, sgk, PP5 and p21$^{Waf1/Cip1}$. These studies revealed that dexamethasone produces a dose-dependent increase in the expression of sgk, which correlates with both an increase in the expression of p21$^{Waf1/Cip1}$ and the hyperphosphorylation of p53 in A549 cells (FIG. 2A). In comparison, the inhibition of PP5 expression with ISIS 15534 produces a similar increase in the phosphorylation of p53 and the expression of p21$^{Waf1/Cip1}$ (FIG. 2B). The effects of ISIS 15534 and dexamethasone appear to be additive for p21$^{Waf1/Cip1}$ mRNA induction (FIG. 2C), and dexamethasone treatment does not appear to change the expression of PP5 mRNA (FIG. 2A). These findings are consistent with the concept that PP5 functions to inhibit both GR and p53 signaling networks leading to the induction of p21$^{Waf1/Cip1}$. Nonetheless, the combined treatment also enhances the expression of sgk (FIG. 2C), raising the possibility that PP5 affects the expression of GR primary response genes. If so, then p53, regulated by reversible phosphorylation, may be a component of the signaling network that is elicited by glucocorticoid hormones and results in p21$^{Waf1/Cip1}$ mediated growth arrest.

Figure 2D:
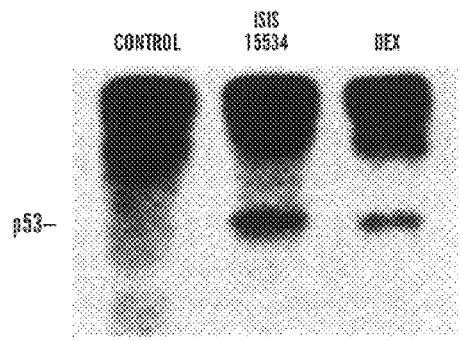
Figure 2E:
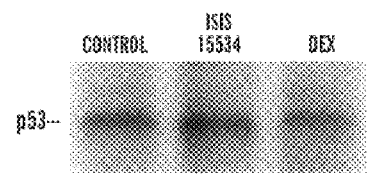

Referring to FIGS. 2A–2C, Northern blot analysis of 549 cells following treatment with dexamethasone and/or ISIS 15534 is shown. Cell cultures in log phase growth were treated with dexamethasone (0–100 nM), ISIS 15534 (0–500 nM), or the combination of dexamethasone (0–100 nM) and ISIS 15534 (500 nM). After 24 hours, 20 μg of total RNA was prepared and analyzed for serine/threonine protein phosphatase 5 (PP5), p21$^{Waf1/Cip1}$ (p21), and serum/glucocorticoid inducible kinase (sgk) mRNA levels. The data shown is representative of three different experiments, and equal loading and transfer of RNA was confirmed by measuring GADPH mRNA levels. Referring to FIG. 2D, hyperphosphorylation of p53 following treatment with ISIS 15534 or dexamethasone is shown. A549 cells were cultured in [$^{32}$P] and treated with 300 nM ISIS 15534, 100 nM dexamethasone (Dex) or vehicle alone (control). Six hours later, the protein extracts were prepared, and changes in p53 phosphorylation were determined by immunoprecipitation, SDS-PAGE analysis, and visualized by autoradiography (Control, p53 from control cells; ISIS 15534, p53 from cells treated with 500 nM ISIS 15534; Dex, p53 from cells treated with 100 nM dexamethasone). Referring to FIG. 2E, a Western analysis of an Immobilon membrane produced by the transfer of protein from the SDS-PAGE gel and detected with an anti-p53 mouse monoclonal antibody is shown.

Figure 3A:
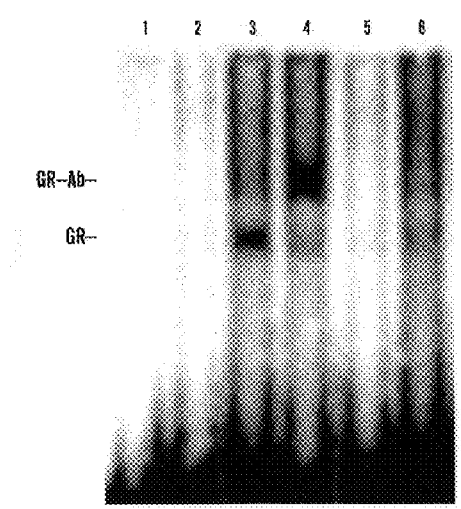
FIGS. 3A–3C illustrate that the inhibition of PP5 expression enhances glucocorticoid receptor binding to DNA.
Figure 3B:
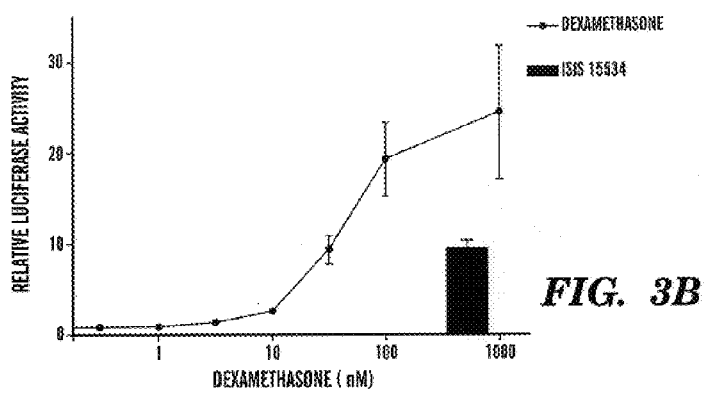
Figure 3C:
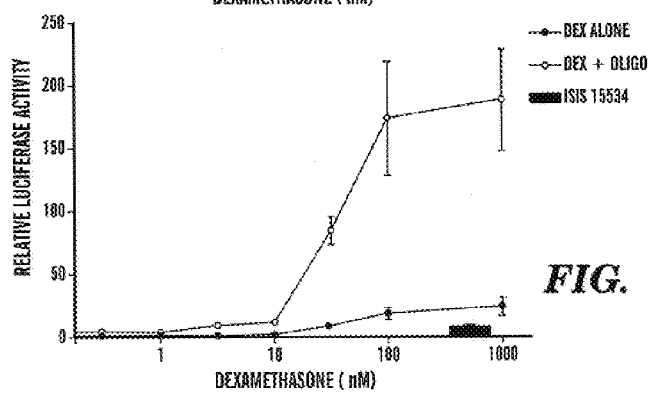

Mobility gel-shift analysis revealed that a marked increase in the association of nuclear GR and DNA containing consensus glucocorticoid recognition elements (GRE) is produced by the inhibition of PP5 expression (FIG. 3A; compare lane 2 with lanes 3 and 4). This occurs even in the absence of dexamethasone, and indicates that the inhibition of PP5 expression does indeed enhance GR/DNA binding. Transient transfection studies conducted with glucocorticoid responsive reporter plasmids demonstrated that the treatment of A549 cells with ISIS 15534 also induces glucocorticoid-mediated transcriptional activation without the addition of dexamethasone (FIG. 3B; compare bar graph with dose response). However, unlike the gel-shift studies where a more pronounced shift is produced by the addition of ISIS 15534 than even 1 μM dexamethasone (FIG. 3A; compare lane 4 and 6), GR-reporter plasmid activation is more pronounced after treatment with ≧100 nM dexamethasone (FIG. 3B). Thus, the inhibition of PP5 expression appears to enhance the association of GR with GRE, while hormone agonist is needed to elicit maximal activation of the transcriptional complex. To test this, cells were treated with dexamethasone 24 hours after the expression of PP5 was inhibited with ISIS 15534. The combined treatment resulted in a dose-dependent increase in GR reporter plasmid activation, with a maximal activation that is about 10 times the maximum response achieved with dexamethasone alone (FIG. 3C). Cumulatively, these findings suggest that PP5 functions as a negative regulator of GR mediated signaling networks, inhibiting hormone induced expression of GR responsive genes.

Referring to FIG. 3A, the inhibition of PP5 expression enhances glucocorticoid receptor binding to DNA. Nuclear extracts were prepared from A549 cell cultures treated with mismatched control oligodeoxynucleotides (ISIS 15521), ISIS 15534, or 1 μM dexamethasone. After 16 hours, the ability of GR to bind DNA was analyzed by gel-mobility shift assay (Li et al. 1991) (Lane 1, no protein control: migration of $^{32}$P-GRE probe in the absence of nuclear extracts; Lane 2, control: nuclear extracts prepared from mismatch control oligodeoxynucleotides treated cells; Lane 3, ISIS 15534-induced gel shift: nuclear extracts from cells treated with 300 nM ISIS 15534; Lane 4, GR-antibody induced supershift: nuclear extracts used in lane 3 after further incubation with an antibody generated against GR (Li et al. 1991); Lane 5, excess cold probe control: samples treated in an identical manner as in lane 3 after incubation in the presence of excess non-radioactive GRE probe; and Lane 6, dexamethasone induced supershift: nuclear extracts from cells treated with 1 µM dexamethasone following incubation with the GR-antibody used in lane 4). Referring to FIG. 3B, stimulation of GRE promoter activity with dexamethasone or ISIS 15534 is shown. A549 cells were transiently transfected with GR luciferase reporter plasmid, MMTV-luc (Jones et al. 1996). Twenty four hours later, the cells were treated with a single dose of the indicated amount of dexamethasone (•) for 2 hours at 37° C., harvested, washed twice with PBS and lysed. Aliquots (150 µl) of cell extracts were then assayed for luciferase activity. The relative light units of the cell extract were calculated as an average of three independent experiments, performed in triplicate, and presented as relative luciferase activity with error bars indicating SD. Luciferase activity in cells treated with 300 nM ISIS 15534 in the absence of dexamethasone is indicated by the solid bar. Referring to FIG. 2C, the inhibition of PP5 expression enhances glucocorticoid stimulation of GR-reporter plasmids. The transient transfection studies described above were repeated with an additional experimental group (○) in which PP5 mRNA expression was inhibited with the addition of 500 nM ISIS 15534 18 hours prior to the addition of dexamethasone. Note the differences in scale on the Y-axis.

Having convincing data showing that PP5 affects both GR- and p53-mediated induction of responsive genes, one then determines if 1) PP5 affects both a p53-mediated signaling pathway and a separate GR-mediated signaling pathway that both lead to the induction of $p21^{Waf1/Cip1}$ and growth arrest, or 2) PP5 inhibits p53 mediated induction of $p21^{Waf1/Cip1}$ by acting upstream of the formation of a functional GR transcriptional complex, in which case GR mediated induction of $p21^{Waf1/Cip1}$ occurs via a p53 dependent mechanism. To explore these possibilities, three cell lines were utilized (one in which growth arrest is induced in response to treatment with dexamethasone or ISIS 15534 and is wild type for p53 (A549) and two others that are p53 defective (T-24 and TR9) and do not undergo growth arrest when treated with dexamethasone or ISIS 15534). Binding studies indicate that all three cell types express GR, and the inhibition of PP5 expression has no apparent effect on the binding of dexamethasone to GR. This suggests that PP5 does not influence the formation of a ligand binding steroid receptor complex. As observed with A549 cells (FIGS. 3B and 3C), transient transfection studies conducted in the T-24 and TR9 cells employing glucocorticoid responsive reporter plasmids revealed that dexamethasone alone, ISIS 15534 alone or the combination of ISIS 15534 and then dexamethasone induces reporter activity in a manner similar to that observed in A549 cells (dexamethasone+ISIS 15534>>>dexamethasone>ISIS 15534). When considered together with the Northern analysis showing that dexamethasone treatment produces the induction of sgk mRNA in all three cell lines (FIG. 1D), it appears that all three cell types express functional GR. Nonetheless, dexamethasone mediated induction of $p21^{Waf1/Cip1}$ mRNA and growth arrest was only evident in the p53 wild type cell lines (FIG. 1D). Therefore, the data suggest that PP5 functions as an inhibitor of GR mediated induction of primary response genes and that GR-induced expression of $p21^{Waf1/Cip1}$ occurs via a p53 dependent pathway. To test this further, antisense oligonucleotides that potently and specifically inhibit the expression of human p53 (ISIS 8345) were developed. When A549 cells are treated with 200 nM ISIS 8345, p53 levels are decreased by about 85%. This correlated with a decrease in dexamethasone induced G1-growth arrest, suggesting that although the induction of p53 gene expression is not necessary for GR-mediated growth inhibition, the presence of the p53 protein is a critical part of GR mediated growth arrest in A549 cells.

Figure 4:
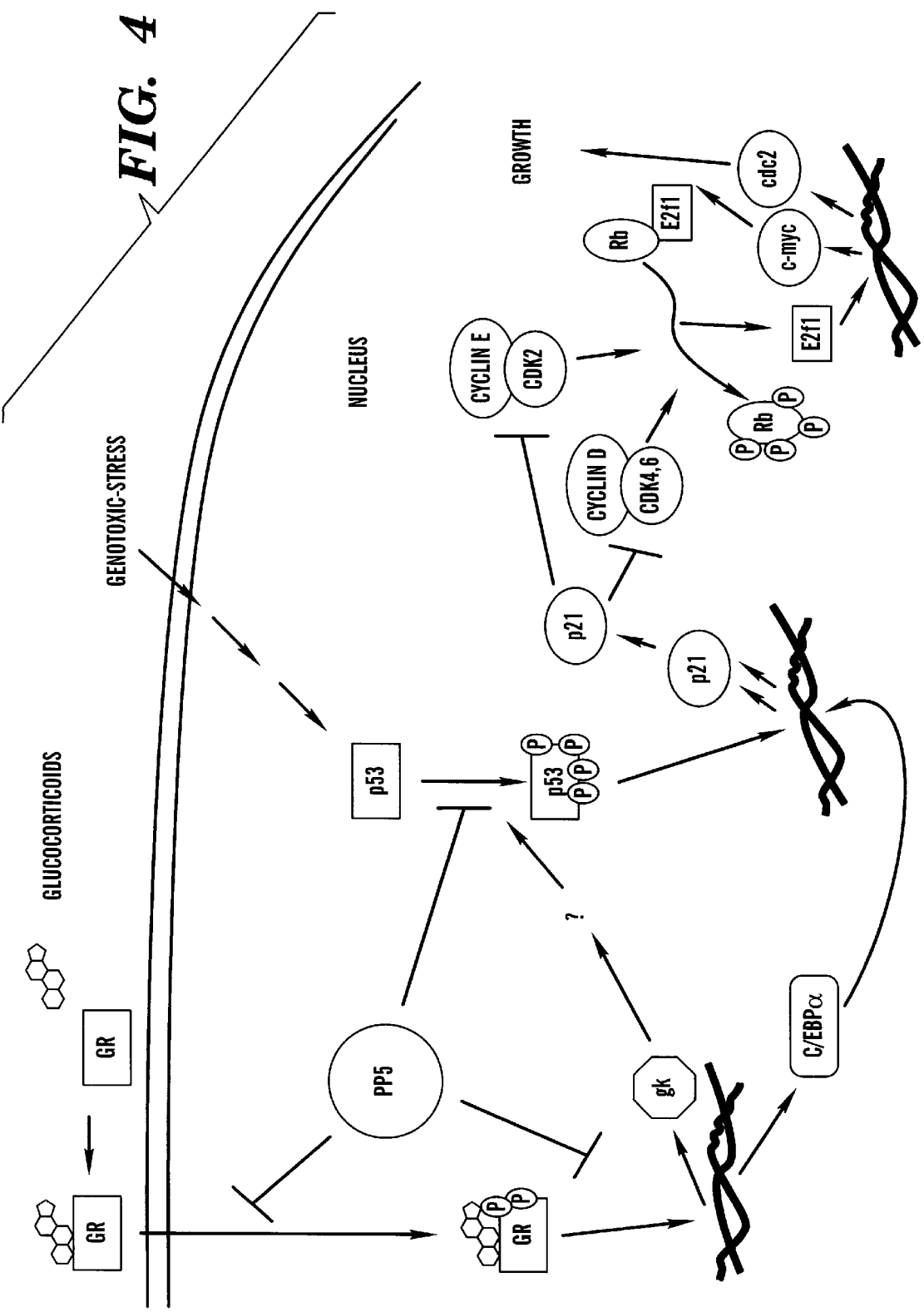
FIG. 4 illustrates the proposed role of PP5 in the regulation of G1-growth arrest initiated by glucocorticoids or genotoxic-stress.

From the data presented here and that available in the literature, PP5 appears to be a critical regulator of cell cycle progression, controlling passage through a p53 dependent G1-checkpoint where signaling cascades elicited by glucocorticoids and stress converge to regulate the induction of $p21^{Waf1/Cip1}$ (FIG. 4).

Referring to FIG. 4, a proposed role of PP5 in the regulation of G1-growth arrest initiated by glucocorticoids or genotoxic-stress is shown. The increase in PP5 expression that occurs during log-phase cell growth functions to inhibit glucocorticoid mediated growth arrest by blocking the association of the ligand activated GR-complex with specific recognition sequences in the promoter of glucocorticoid responsive genes and/or the formation of an active GR-transcriptional complex. This inhibits the expression of a GR-inducible protein kinase (gk) or a signal transduction cascade that results in the activation of a kinase, which catalyzes the phosphorylation of p53. In the absence of PP5, the hyperphosphorylation of p53 produces a form of p53 with increased transcriptional activity, allowing the basal amount of p53 to induce the expression of the cyclin/CDK inhibitor protein (p21). p21 inhibits the activity of G1-cyclin/CDK complexes (Cyclin D/CDK4,6; Cyclin E/CDK2). In turn, this prevents the hyperphosphorylation of the Rb-tumor suppressor protein and facilitates G1 cell cycle arrest. In response to genotoxic stress, the amount of p53 increases may be due to a decrease in degradation rate and, in some instances, an increase in p53 expression. In the presence of PP5, the increased amount of p53 is needed to "override" the growth promoting effects of PP5. In some cells PP5 may have a dual role: 1) acting directly to catalyze the dephosphorylation of p53 and 2) acting to inhibit the expression of proteins, such as the CEBPA, that appear to participate in the glucocorticoid-dependent, p53-independent induction of p21.

In addition to a possible direct effect on p53, in A549 cells PP5 prevents the phosphorylation of p53 by inhibiting the expression of a GR inducible p53 kinase or a GR inducible signaling cascade that culminates in the hyperphosphorylation of p53. Thus, the hyperphosphorylation of a relatively small amount of constitutively expressed p53 appears to be sufficient for the propagation of a steroid hormone induced signaling cascade that inhibits cell growth, while both enhanced phosphorylation and enhanced expression of p53 contribute to the propagation of a DNA damage induced response (Levine 1997; Agarwal et al. 1998). Although the data suggest that p53 is a necessary component of a signaling cascade elicited by glucocorticoids that leads to G1-growth arrest, it does not exclude the existence of additional GR-induced mechanisms that lead to the induction of $p21^{Waf1/Cip1}$. Indeed, since high concentrations ($\geq$100 nM) of dexamethasone can still partially inhibit A549 cell growth even when the expression of p53 is suppressed with ISIS 8345, it is tempting to speculate that cells which are acutely sensitive to the antiproliferative effects of glucocorticoids derive their acute sensitivity from a synergistic effect where dexamethasone induces the expression of $p21^{Waf1/Cip1}$ by both p53 dependent and p53 independent (Cram et al. 1998) mechanisms. Furthermore, because the data suggest that PP5 is a key negative regulator of glucocorticoid-mediated induction of $p21^{Waf1/Cip1}$, the increased expression of PP5 that is observed during log phase growth may prove important for the regulation of cellular proliferation. That is, by inhibiting GR-mediated growth arresting pathways, an increase in PP5 expression may facilitate the actions of growth promoting compounds. Alternatively, increased PP5 expression may result in the abatement of glucocorticoid maintained growth arrest, and, thus, induce, or contribute to the initiation of, a proliferative response. Either way, this suggests that aberrations in the regulation of PP5 expression may contribute to neoplastic transformation and is consistent with 1) the observation that PP5 expression is higher in tumor cells than in "normal" differentiated cells; and 2) that the inhibition of PP5 expression alone inhibits cell growth in p53 wild-type tumor cells (Zuo et al. 1998). More importantly, since mutations in p53 are associated with about 50% of all human cancers, the data presented here demonstrating that p53 participates in GR-hormone induced G1-growth arrest suggest that the loss of glucocorticoid-induced growth arrest may be an important component of the aberrant proliferative behavior of p53 defective tumor cells. Clinically the presence or absence of functional p53 may provide insight into why some hematologic malignancies respond to GR treatment, while others with a similar phenotype do not. If so, the p53 status of a cancer cell may also prove predictive for determining the effectiveness of glucocorticoid incorporation into the chemotherapy regimen used in the treatment of GR-responsive cancers. Compounds that inhibit PP5 activity may also have significant therapeutic value in the treatment of patients with defects in glucocorticoid signaling pathways or pathways involved in p53 signaling.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 2-continued

| ISIS # | Sequence | Backbone | SEQ ID NO: |
|---|---|---|---|
| 15521 | GTGCGATCGTTGCGGTTAGC | P = O/P = S | 14 |

TABLE 3

| ISIS # | Sequence | Backbone | SEQ ID NO: |
|---|---|---|---|
| 14493 | TCGCCCTCCGCCATTCGCCAT | P = O/P = S | 1 |
| 15516 | TCGCCCTCCGCCATCGCCAT | P = S | 1 |
| 15517 | GCTCTACTCCGCCCCATGCC | P = O/P = S | 15 |

REFERENCES

Agarwal, M. L., et al., Proc Natl Acad Sci USA 92:8493–8497 (1995).
Agarwal, M. L., et al., J Biol Chem 273:1 (1998).
Ammala et al., Proc Natl Acad Sci USA 91:4343–4347 (1994).

TABLE 1

Human PP5 Antisense Oligonucleotides

| Isis # | Sequence (5' → 3') | Target source and site (Genbank #; nucleotide #s) | Target region | Percent Inhibition | SEQ ID NO: |
|---|---|---|---|---|---|
| 14493 | TCGCCCTCCGCCATCGCCAT | x92121; nt 70–89; AUG | AUG | 84% | 1 |
| 14494 | TTCAGAGCTCCATCAGCCGG | x92121; nt 127–146; | coding | 52 | 2 |
| 14495 | GTAGGCCAGGCTGCGGTTGC | u25174; nt 175–194; | coding | 66 | 3 |
| 14496 | CCGCTGTACTCATCCTCAAT | u25174; nt 492–511; | coding | 54 | 4 |
| 14497 | TCCCCACATACTGTAATCTT | u25174; nt 684–703; | coding | 11 | 5 |
| 14498 | GTACTTGGCCTTCACCTCAC | x89416; nt 933–952; | coding | 80 | 6 |
| 14499 | CCAGGTTGTTCTCTTCCAAG | x89416; nt 1225–1244; | coding | 62 | 7 |
| 14500 | AGAGCCCTGGAGGTGGATGT | x89416; nt 1365–1384; | coding | 41 | 8 |
| 14501 | CGCCCCGCCCGTCACCTCAC | x89416; nt 1480–1499; | Stop codon | 42 | 9 |
| 14502 | CCTACCCCCTCTGCAAACCT | x89416; nt 1625–1644; | 3'UTR | 40 | 10 |
| 14503 | GCCCCAGCTGCTCCACCTCC | x89416; nt 1694–1713; | 3'UTR | 27 | 11 |
| 14504 | GGGCCCTATTGCTTGAGTGG | x89416; nt 1810–1829; | 3'UTR | 92 | 12 |
| 14505 | CCCAGCCTAGCCCCACCATG | x89416; nt 1899–1918; | 3'UTR | 23 | 13 |

TABLE 2

| ISIS # | Sequence | Backbone | SEQ ID NO: |
|---|---|---|---|
| 15523 | GGGCCCTATTGCTTGAGTGG | P = S | 12 |
| 15534 | GGGCCCTATTGCTTGAGTGG | P = O/P = S | 12 |

Baserga, R., and T. Ashihara, Methods in Enzymology LVIII:248–262 (1979).
Berge et al., J Pharma Sci 66:1 (1977).
Cairns et al., J Biol Chem 269:9176–9183 (1994).
Chernov, M. V., et al., Proc Natl Acad Sci USA 95:2284 (1998).
Chiang et al., J Biol Chem 266:18162–18167 (1991).
Cram, E. J., et al., J Biol Chem 273:2008–2014 (1998).
De Mesmaeker et al., Acc Chem Res 28:366–374 (1995).
Dean, N. M., and R. G. Griffey, Antisense Nucl Acid Drug Dev 7:229–233 (1997).

Dean, N. M., et al., J Biol Chem 269:16416–16424 (1994).
Gebeyehu, G., et al., Nucl Acids Res 15:4513 (1987).
Honkanen, R. E., et al., J Biol Chem 266:6614–6619 (1991).
Jones, L. C., et al., Endocrinology 137:3815–3822 (1996).
Kabanov et al., FEBS Lett 259:327 (1990).
Kawasaki et al., J Med Chem 36:831–841 (1993).
Kornberg, A., "DNA Replication", W.H. Freeman & Co., San Francisco, pp 75–77 (1980).
Letsinger et al., Proc Natl Acad Sci USA 86:6553 (1989).
Levine, A. J., Cell 88:323 (1997).
Li, Y. C., et al., Mol Cell Biol 11:1883–1893 (1991).
Maiyar, A. C., et al., J Biol Chem 271:12414 (1996).
Manoharan et al., Ann NY Acad Sci 660:306 (1992).
Manoharan et al., Bioorg Med Chem Let 3:2765 (1993).
Manoharan et al., Bioorg Med Chem Let 4:1053 (1994).
Manoharan et al., Nucleosides & Nucleotides 14:969 (1995a).
Manoharan et al., Tetrahedron Lett 36:3651 (1995b).
Martin, P., Helv Chim Acta 78:486–504 (1995).
Nielsen et al., Science 254:1497 (1991).
Oberhauser et al., Nucl Acids Res 20:53 (1992).
Orth, D. N., et al., in "Williams Textbook of Endocrinology", Wilson, J. D. and D. W. Foster, Eds., W.B. Saunders Company, Philadelphia, pp. 570–575 (1992).
Reynolds, P. D., et al., J Clin Endocrinol Metab 82:465 (1997).
Saison-Behmoaras et al., EMBO J 10:111 (1991).
Sambrook et al., "Molecular Cloning. A Laboratory Manual", Cold Spring Harbor Laboratory Press, Volume 2, pg 11.31–11.32 (1989).
Sanghvi, Y. S., in Crooke, S. T. and Lebleu, B., eds., "Antisense Research and Applications", CRC Press, Boca Raton, pp 276–278 (1993).
Sanghvi et al., Nucl Acids Res 21:3197–3203 (1993).
Schimmer, B. P. and K. L. Parker, in "Goodman & Gilman's The Pharmacological Basis of Therapeutics", 9th Ed., Hardman, J. G., et al., Eds., McGraw-Hill, New York, pp 1465–1481 (1996).
Svinarchuk et al., Biochimie 75:49 (1993).
Webster, M. K., et al., Mol Cell Biol 13:2031 (1993).
Wera and Hemmings, Biochem J 311:17–29 (1995).
Zuo, Z., et al., J Biol Chem 273:12250 (1998).

What is claimed is:

1. A composition comprising a glucocorticoid receptor agonist and a compound which decreases levels of active human serine/threonine protein phosphatase 5 protein in in vitro cells.

2. The composition of claim 1 wherein the compound decreases levels of active human serine/threonine protein phosphatase 5 protein by decreasing PP5 gene expression of the PP5 protein in the in vitro cells.

3. The composition of claim 2 wherein the compound is an antisense oligonucleotide targeted to a nucleic acid encoding human serine/threonine protein phosphatase 5.

4. The composition of claim 3, wherein the antisense oligonucleotide is about 8 to 50 nucleotides in length.

5. The composition of claim 3 wherein the antisense oligonucleotide is targeted to a translation initiation site, coding region, or 3' untranslated region of mRNA encoding the human serine/threonine protein phosphatase 5.

6. The composition of claim 1 wherein the compound is an inhibitor of the PP5 protein.

7. The composition of claim 1 wherein the glucocorticoid receptor agonist is dexamethasone.

* * * * *

SEQUENCE LISTING

<160> NUMBER OF SEQ ID NOS: 22

<210> SEQ ID NO: 1
<211> LENGTH: 20
<212> TYPE: DNA
<213> ORGANISM: Homo sapiens

<400> SEQUENCE: 1
tcgccctccg ccatcgccat                                           20

<210> SEQ ID NO: 2
<211> LENGTH: 20
<212> TYPE: DNA
<213> ORGANISM: Homo sapiens

<400> SEQUENCE: 2
ttcagagctc catcagccgg                                           20

<210> SEQ ID NO: 3
<211> LENGTH: 20
<212> TYPE: DNA
<213> ORGANISM: Homo sapiens

<400> SEQUENCE: 3
gtaggccagg ctgcggttgc                                           20

<210> SEQ ID NO: 4
<211> LENGTH: 20
<212> TYPE: DNA
<213> ORGANISM: Homo sapiens

<400> SEQUENCE: 4
ccgctgtact catcctcaat                                           20

<210> SEQ ID NO: 5
<211> LENGTH: 20
<212> TYPE: DNA
<213> ORGANISM: Homo sapiens -continued

```
<400> SEQUENCE: 5
tccccacata ctgtaatctt                                              20

<210> SEQ ID NO: 6
<211> LENGTH: 20
<212> TYPE: DNA
<213> ORGANISM: Homo sapiens

<400> SEQUENCE: 6
gtacttggcc ttcacctcac                                              20

<210> SEQ ID NO: 7
<211> LENGTH: 20
<212> TYPE: DNA
<213> ORGANISM: Homo sapiens

<400> SEQUENCE: 7
ccaggttgtt ctcttccaag                                              20

<210> SEQ ID NO: 8
<211> LENGTH: 20
<212> TYPE: DNA
<213> ORGANISM: Homo sapiens

<400> SEQUENCE: 8
agagccctgg aggtggatgt                                              20

<210> SEQ ID NO: 9
<211> LENGTH: 20
<212> TYPE: DNA
<213> ORGANISM: Homo sapiens

<400> SEQUENCE: 9
cgccccgccc gtcacctcac                                              20

<210> SEQ ID NO: 10
<211> LENGTH: 20
<212> TYPE: DNA
<213> ORGANISM: Homo sapiens

<400> SEQUENCE: 10
cctaccccct ctgcaaacct                                              20

<210> SEQ ID NO: 11
<211> LENGTH: 20
<212> TYPE: DNA
<213> ORGANISM: Homo sapiens

<400> SEQUENCE: 11
gccccagctg ctccacctcc                                              20

<210> SEQ ID NO: 12
<211> LENGTH: 20
<212> TYPE: DNA
<213> ORGANISM: Homo sapiens

<400> SEQUENCE: 12
gggccctatt gcttgagtgg                                              20

<210> SEQ ID NO: 13
<211> LENGTH: 20
<212> TYPE: DNA
<213> ORGANISM: Homo sapiens
```

```
<210> SEQ ID NO: 13

<400> SEQUENCE: 13
cccagcctag ccccaccatg                                               20

<210> SEQ ID NO: 14
<211> LENGTH: 20
<212> TYPE: DNA
<213> ORGANISM: Homo sapiens

<400> SEQUENCE: 14
gtgcgatcgt tgcggttagc                                               20

<210> SEQ ID NO: 15
<211> LENGTH: 20
<212> TYPE: DNA
<213> ORGANISM: Homo sapiens

<400> SEQUENCE: 15
gctctactcc gccccatgcc                                               20

<210> SEQ ID NO: 16
<211> LENGTH: 35
<212> TYPE: DNA
<213> ORGANISM: Homo sapiens

<400> SEQUENCE: 16
atggcgatgg cggagggcga gaggactgag tgtgc                              35

<210> SEQ ID NO: 17
<211> LENGTH: 26
<212> TYPE: DNA
<213> ORGANISM: Homo sapiens

<400> SEQUENCE: 17
tcacatcatt cctagcacca gcagcg                                        26

<210> SEQ ID NO: 18
<211> LENGTH: 24
<212> TYPE: DNA
<213> ORGANISM: Homo sapiens

<400> SEQUENCE: 18
atgtcagaac cggctgggga tgtc                                          24

<210> SEQ ID NO: 19
<211> LENGTH: 24
<212> TYPE: DNA
<213> ORGANISM: Homo sapiens

<400> SEQUENCE: 19
gggcttcctc ttggagaaga tcag                                          24

<210> SEQ ID NO: 20
<211> LENGTH: 20
<212> TYPE: DNA
<213> ORGANISM: Homo sapiens

<400> SEQUENCE: 20
ccagaatgcc agaggctgct                                               20

<210> SEQ ID NO: 21
<211> LENGTH: 20
<212> TYPE: DNA
<213> ORGANISM: Homo sapiens
```

-continued

```
<400> SEQUENCE: 21
tcatccaaat actccacacg                                              20

<210> SEQ ID NO: 22
<211> LENGTH: 27
<212> TYPE: DNA
<213> ORGANISM: Homo sapiens

<400> SEQUENCE: 22
agaggatctg tacaggatgt tctagat                                      27
```